United States Patent
Roser

[19]

[11] Patent Number: 6,102,896
[45] Date of Patent: Aug. 15, 2000

[54] DISPOSABLE INJECTOR DEVICE

[75] Inventor: Bruce Joseph Roser, Cambridge, United Kingdom

[73] Assignee: Cambridge Biostability Limited, Cambridge, United Kingdom

[21] Appl. No.: 09/392,293

[22] Filed: Sep. 8, 1999

[51] Int. Cl.[7] .................................................. A61M 5/00
[52] U.S. Cl. .......................... 604/218; 604/124; 604/232
[58] Field of Search .................................. 604/218, 110, 604/201–205, 207, 210, 232, 187, 136, 137, 123, 124

[56] References Cited

U.S. PATENT DOCUMENTS

| | | | |
|---|---|---|---|
| 2,704,542 | 3/1955 | Scherer | 128/173 |
| 3,407,956 | 10/1968 | Linkletter et al. | 215/41 |
| 3,908,651 | 9/1975 | Fudge | 128/173 |
| 3,998,224 | 12/1976 | Chiquiar-Arias | 128/218 |
| 4,013,073 | 3/1977 | Cunningham | 128/216 |
| 4,018,222 | 4/1977 | McAleer et al. | 128/216 |
| 4,233,975 | 11/1980 | Yerman | 128/218 |
| 4,391,272 | 7/1983 | Staempfli | 604/110 |
| 4,698,318 | 10/1987 | Vogel et al. | 501/10 |
| 4,793,997 | 12/1988 | Drake et al. | 424/426 |
| 4,866,097 | 9/1989 | Drake et al. | 514/770 |
| 4,891,319 | 1/1990 | Roser | 435/188 |
| 4,966,581 | 10/1990 | Landau | 604/72 |
| 5,589,167 | 12/1996 | Cleland et al. | 424/85.7 |
| 5,746,714 | 5/1998 | Salo et al. | 604/68 |

FOREIGN PATENT DOCUMENTS

| | | |
|---|---|---|
| 0595508 | 4/1994 | European Pat. Off. . |
| 0879609 | 11/1998 | European Pat. Off. . |
| WO90/11756 | 10/1990 | WIPO . |
| WO98/15307 | 4/1998 | WIPO . |
| WO98/17332 | 4/1998 | WIPO . |
| WO98/41188 | 9/1998 | WIPO . |

OTHER PUBLICATIONS

L. Jodar et al, Genetic Engineering News, "Revolutionizing Immunizations", Feb. 15, 1998, pp. 1–5.
P. Johansen et al, Proceed. Int'l. Symp . . . , vol. 25, "Albumin Improves The Delivery . . . ", 1998, pp. 633–634.
J. Lloyd et al, World Health Organization, "Pre–Filled Monodose Injection Devices . . . ", May 1998, pp. 1–23.
E.M. Gribbon et al, Stabilisation of Vaccines Using Trehalose (Q–T4) Technology, 1996, pp. 1–12.
E.M. Gribbon et al, "Q–T4 Stabilization and Novel Drug Delivery Formats", 1995, 4 pages.
Camilo Colaco et al, Bio/Technology, vol. 10, "Extraordinary Stability of Enzymes . . . ", Sep. 10, 1992, pp. 1007–1011.

*Primary Examiner*—John D. Yasko
*Attorney, Agent, or Firm*—Jacobson, Price, Holman & Stern, PLLC

[57] ABSTRACT

The present invention is a single use injector device for injecting parenteral medications which operates by hand force. The injector device has a plunger section and a base. As hand force is applied to a moving portion of the plunger section, break tabs or a snap ring resist its motion toward the patient's skin surface. The break tabs or snap ring release abruptly as the hand force reaches a snap point. The motion of the moving portion then drives the medication through the skin surface and into the body of the patient. If the medication is in liquid form, the actual injection may be carried out through a hollow needle attached to the plunger section. Alternatively, the suddenly increased pressure of the medication at the snap point may be used to form a liquid jet for needleless injection. Part or all of the medication may be contained in a glass needle which dissolves in the body after injection. The injector device requires little training to use, reduces perceived pain, and improves injection safety.

49 Claims, 11 Drawing Sheets

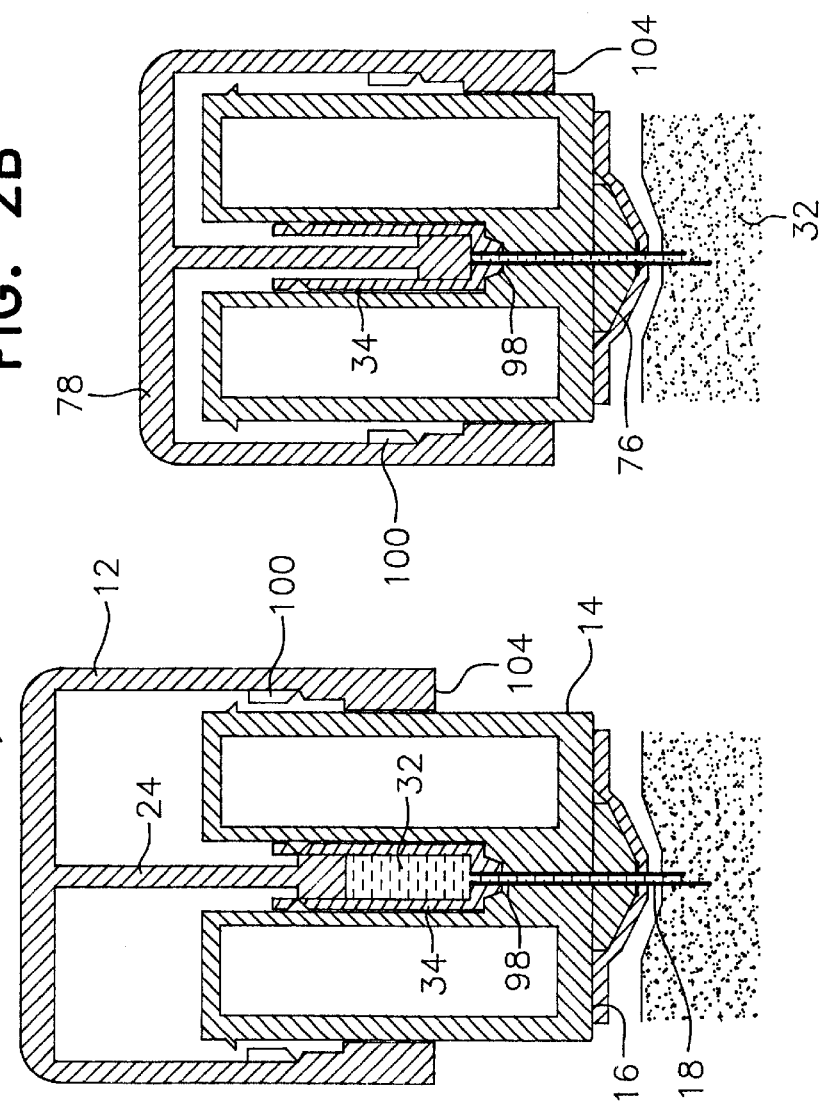

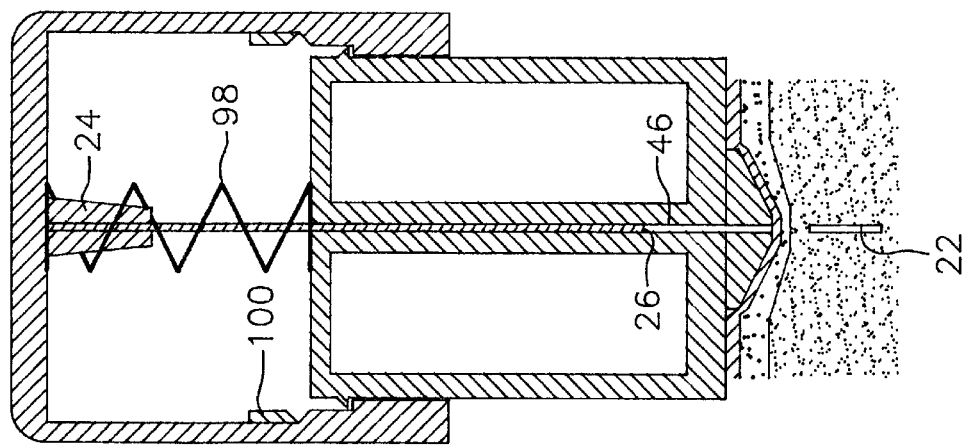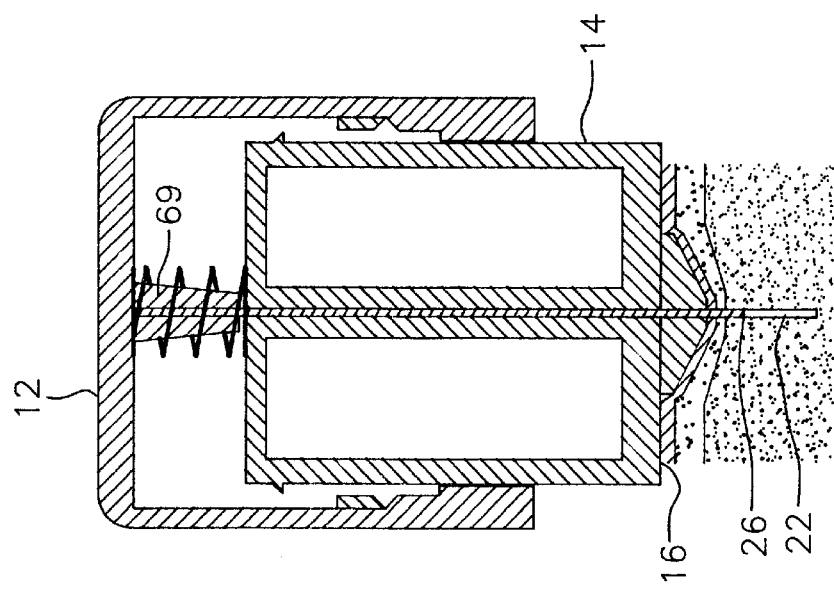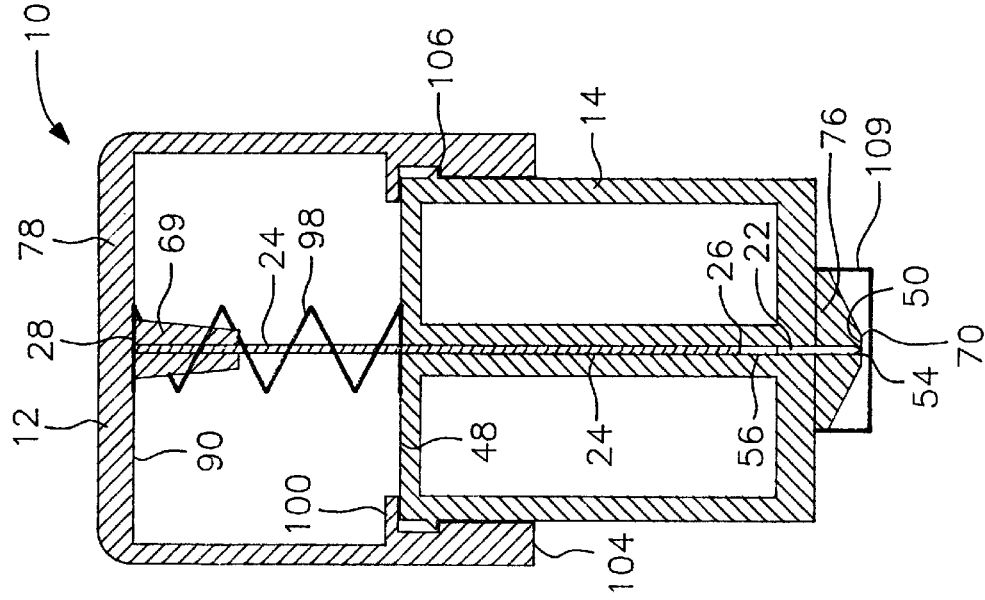

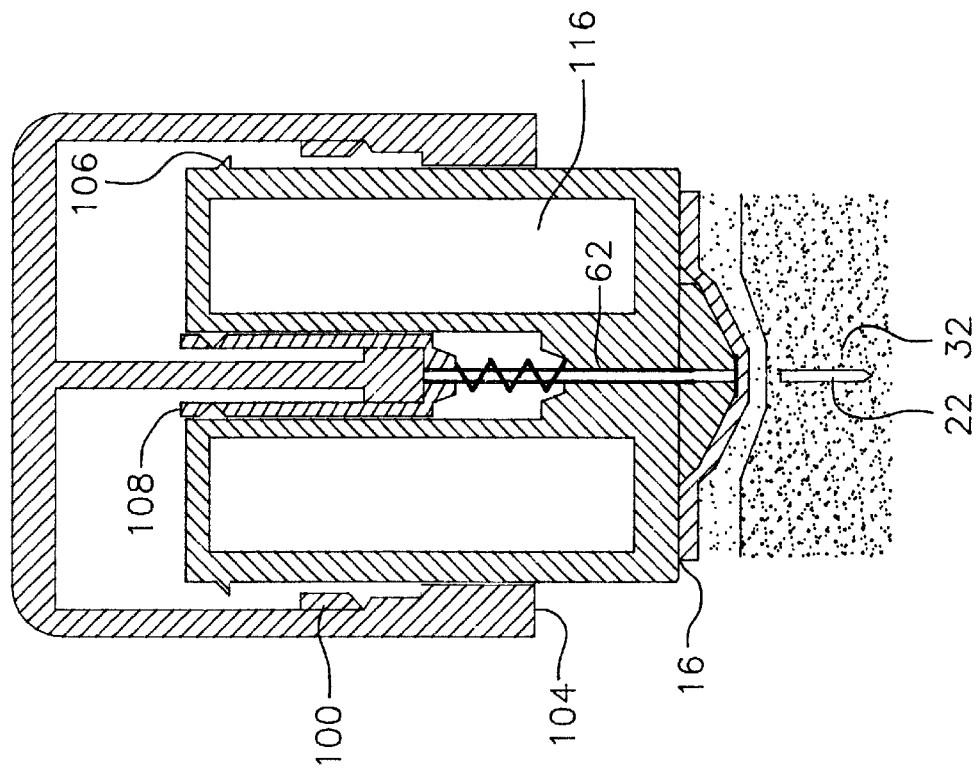
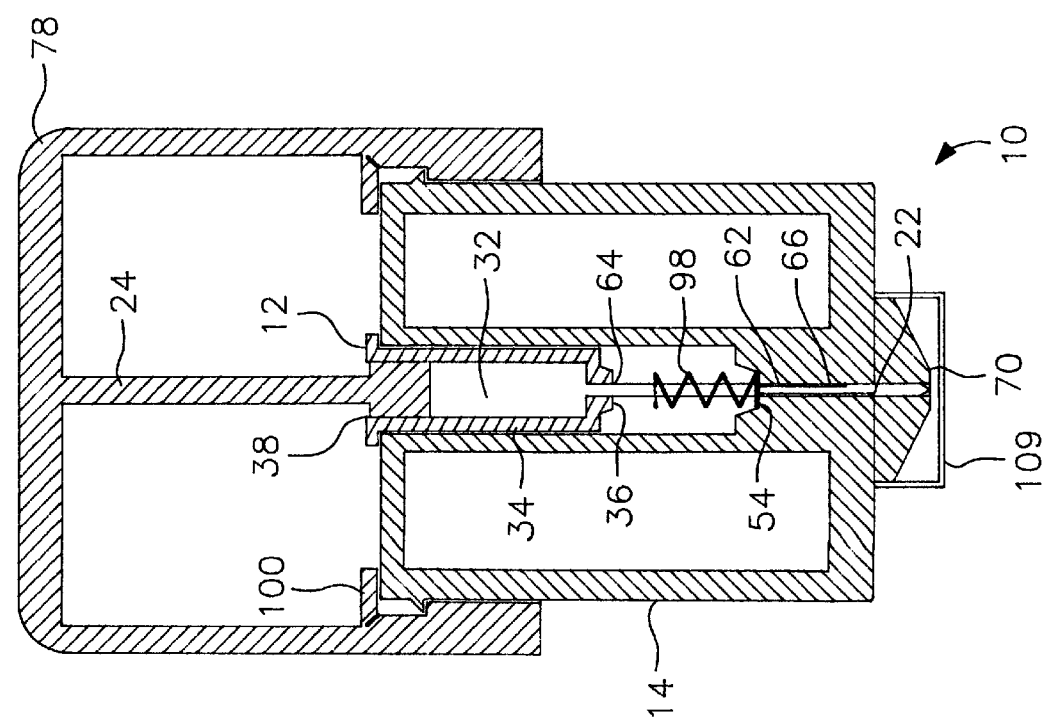
FIG. 4B
FIG. 4A

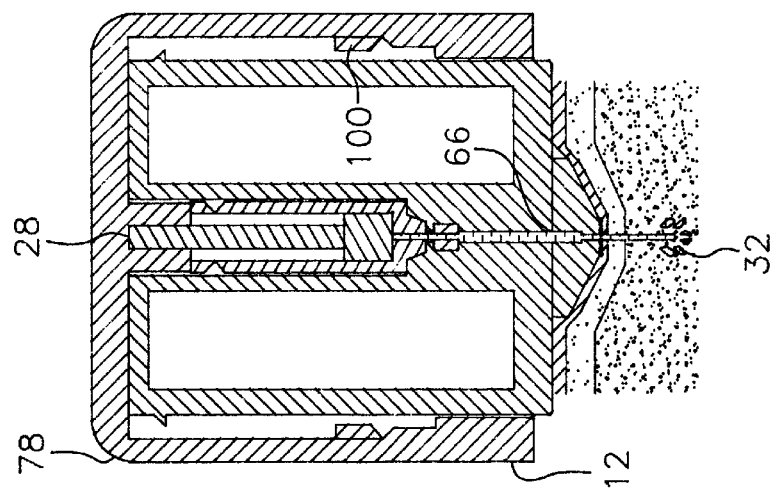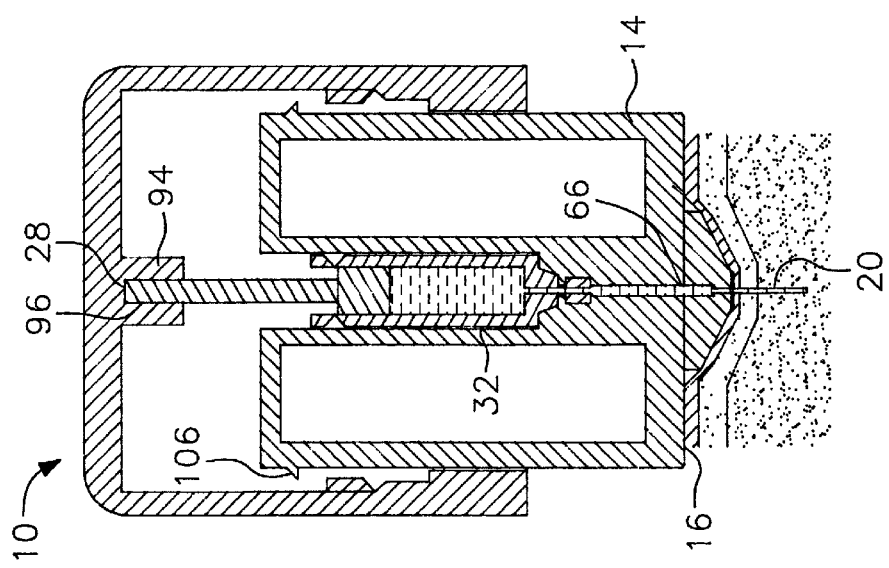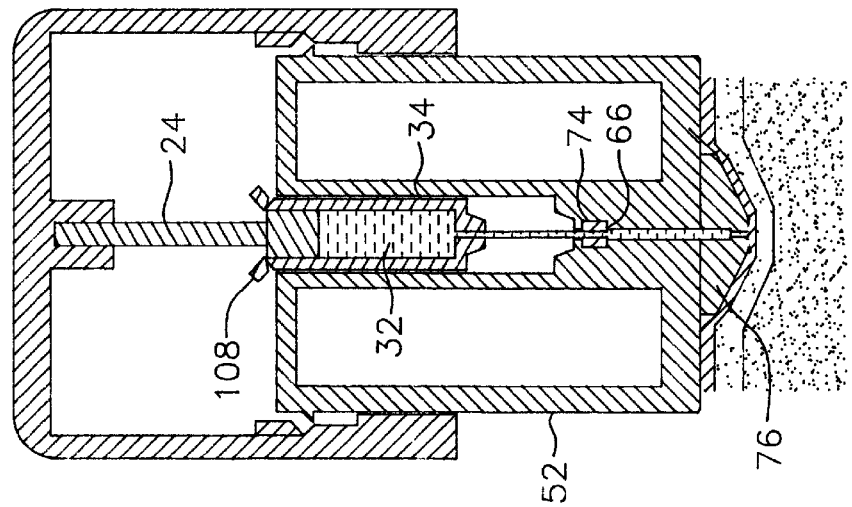

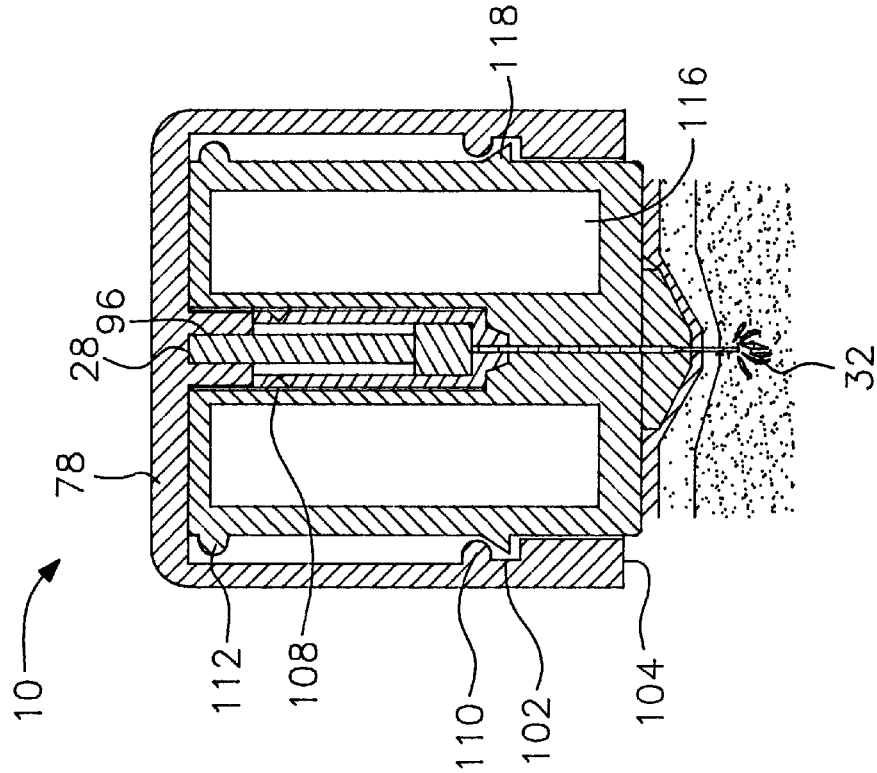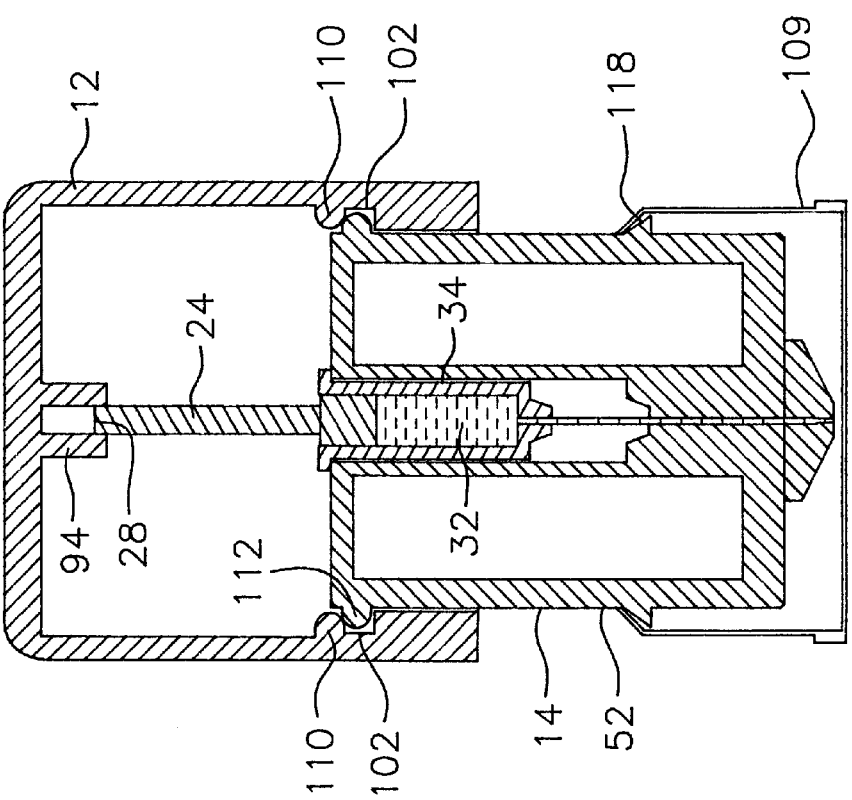

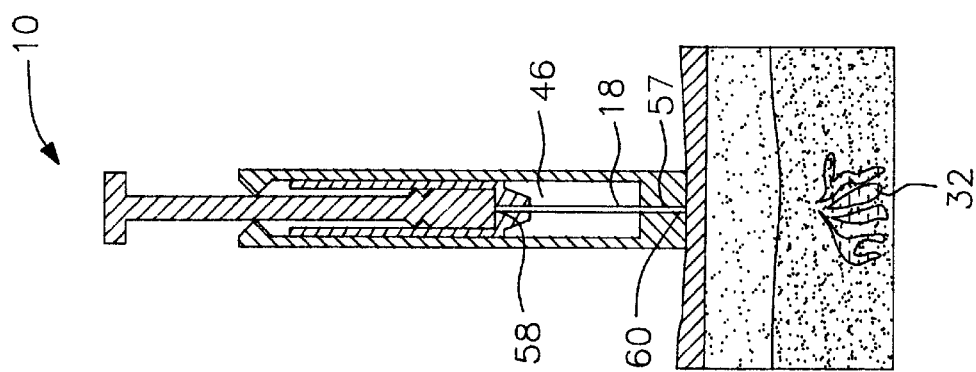
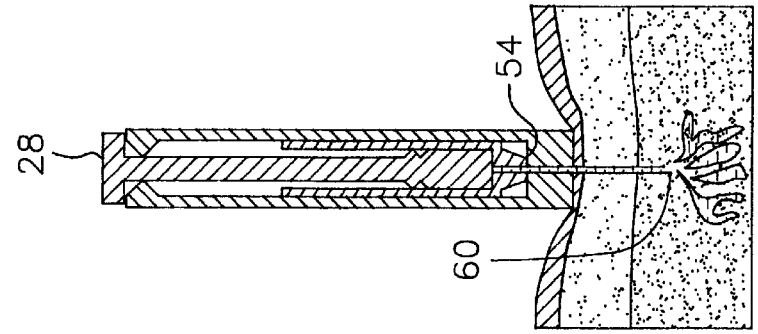
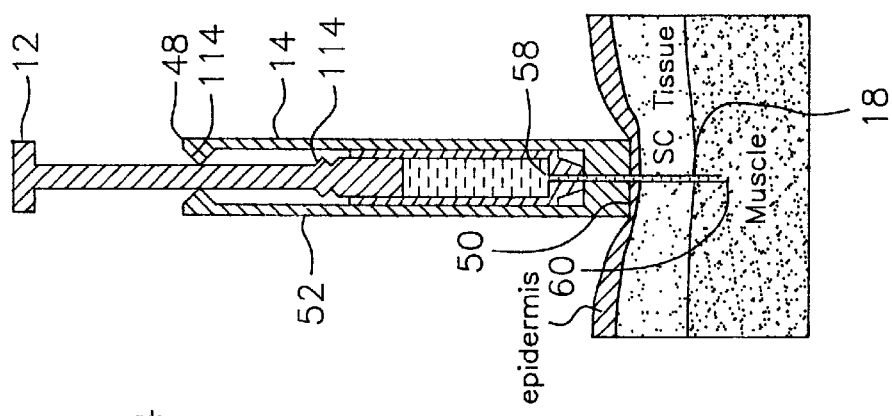
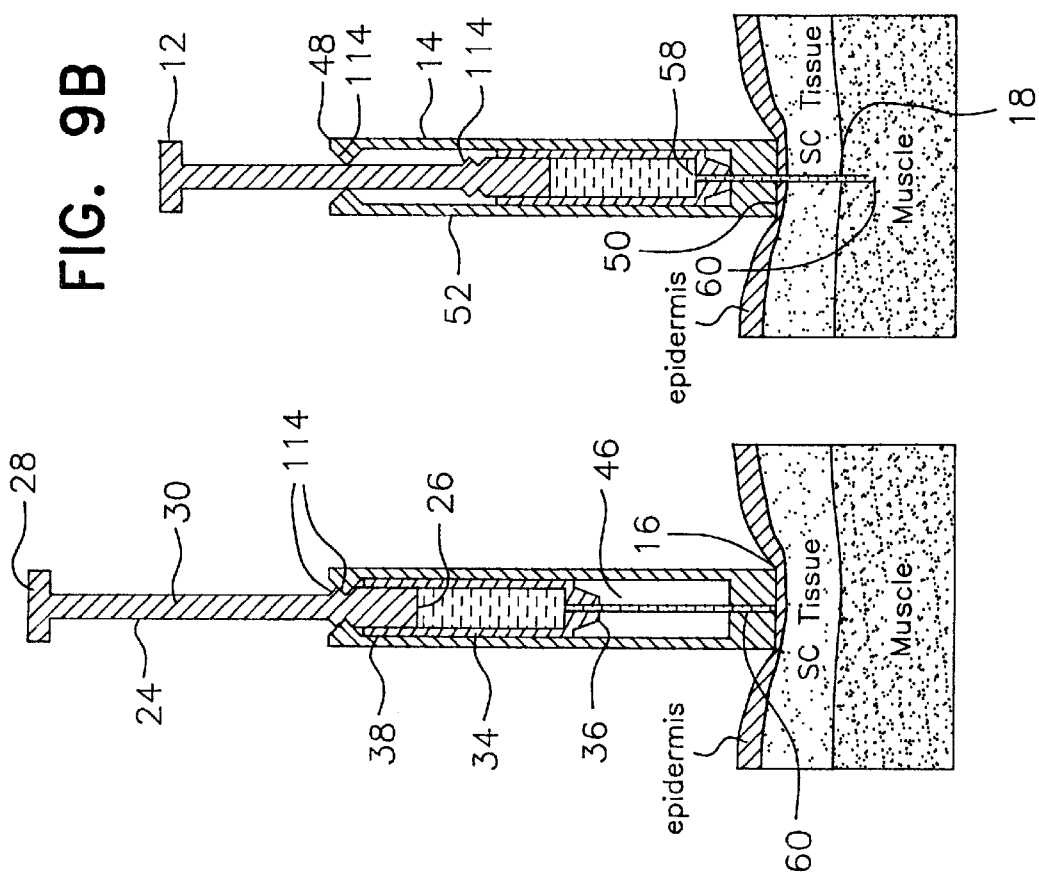

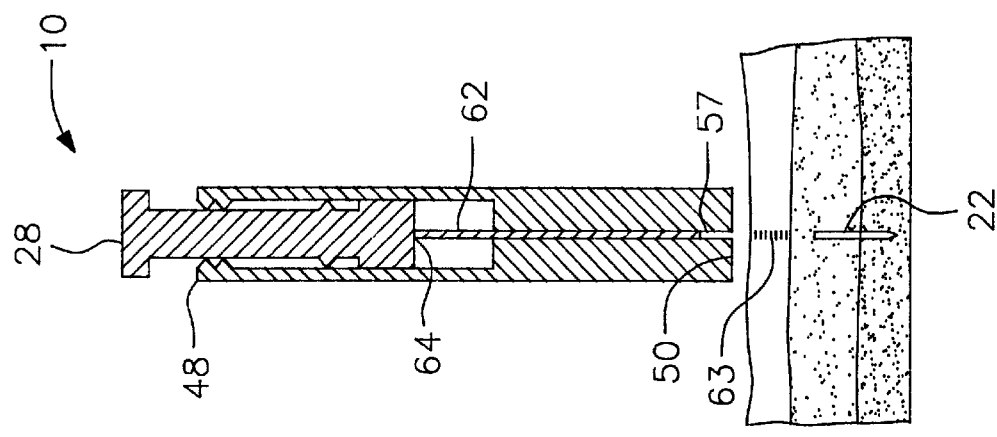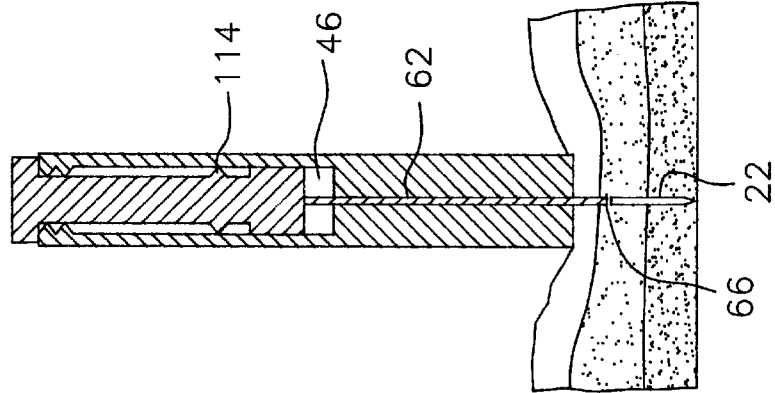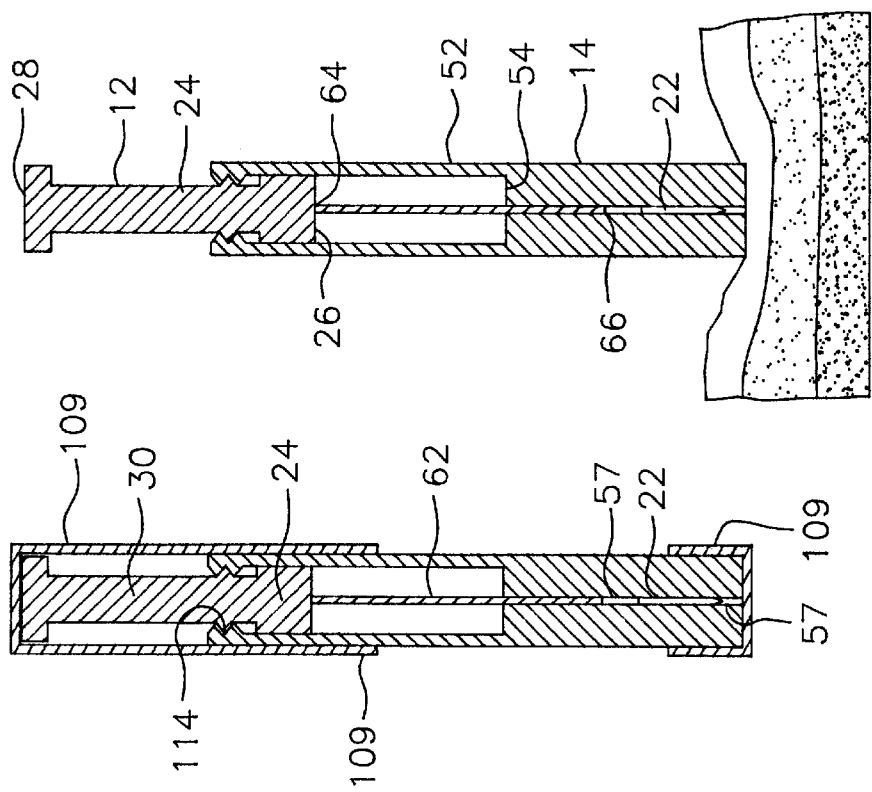

DISPOSABLE INJECTOR DEVICE

FIELD OF THE INVENTION

This invention is directed generally to injector devices, and specifically to a disposable injector device operating by hand force and having a snap means such as break tabs or a snap ring to release the plunger section abruptly as a snap point is reached.

BACKGROUND OF THE INVENTION

Although modern vaccines and drugs are effective in controlling disease, there are serious problems with parenteral injections. The use of the standard hollow metal needle attached to a syringe is inherently cumbersome. The usual process of giving an injection involves performing all the following steps using sterile technique:

1. Take the freeze-dried drug, in its rubber-capped glass vial, from the refrigerator and remove the sterile cap.
2. Take and prepare a similar vial of sterile water for injection (WFI) from its box.
3. Remove a wide-bore needle from its sterile packaging.
4. Remove a sterile disposable syringe from its sterile packaging.
5. Attach the needle to the syringe.
6. Use the syringe and needle to aspirate a precise volume of sterile WFI.
7. Use the syringe and needle to deliver this WFI into the vial containing the freeze-dried drug.
8. Swirl or shake the vial until the dried drug is completely dissolved.
9. Use the syringe and needle to aspirate the required dose back into the syringe.
10. Remove a narrow bore needle from its sterile packaging.
11. Replace the used wide bore needle used in 5–9 above with the fresh narrow bore needle for injection.
12. Carefully expel all the air from the syringe and needle.
13. Inject the drug.

This tedious process can only be reliably undertaken by medically trained personnel. The risks of incorrect dilution or dose measurement are obvious. Any failure of sterile technique can lead to dangerous infections. The danger is greater if the reconstituted drug or vaccine is stored for any length of time before it is used. The final injection step also requires training and practice to achieve the correct depth and the dexterity to deliver the injection quickly and with minimal pain. These skills are not in abundant supply. The lack of trained personnel actually constrains current, immunization campaigns.

Most syringes and needles today are designed to be disposable. However, such disposable syringes are in fact routinely re-used, both in the developing world and by drug addicts in the developed world. Typically the cleaning and sterilization techniques used are inadequate, leading to serious risks of infection and cross-contamination.

An additional problem with parenteral injections is that only a few drugs or vaccines are available in the form of injection-ready, stable liquids. The great majority of parenteral preparations are freeze-dried and require dilution before injection. The great majority also require constant refrigeration during storage.

Patient compliance with immunization protocols is also a serious difficulty faced by public health authorities. When standard syringes and needles are used, patients often do not return to field stations for follow-up doses. This is particularly true for infants, who must undergo a series of injections. Injections are perceived by patients as very painful, though in actuality the pain experienced during insertion of a properly sharp and well lubricated needle is not very severe. Much of the perceived pain is actually anxiety, caused by the sight of the needle, especially as it enters the flesh. This can be so severe as to cause patients to fail to complete a course of immunization.

Present needle technology also present problems for health workers, who are at risk from infection due to accidental needle sticks. When improperly discarded, conventional needles and syringes also present a health hazard to the local population.

Present parenteral injection technology has recently been deemed by the World Health Organization (WHO) to be incompatible with their requirements for the planned Global Programme of Vaccination and Immunization (GPV) initiatives. It is estimated that 6 additional parenteral vaccines will be recommended for childhood vaccination by the year 2005, requiring a total of 3.6 billion immunization injections per year. The total number of parenteral injections, including injected drugs as well as vaccines, will be roughly ten times this number. Major health care providers such as UNICEF, the WHO and CDC have recently confirmed that a radical new technology is required that can be used by personnel with minimal training and that is safer, more convenient, and more comfortable than the syringe and needle. (Jodar L., Aguado T., Lloyd J. and Lambert P-H,(1998) Revolutionizing Immunizations Gen. Eng. News 18, p. 6.) The criteria required by the WHO for the next generation of vaccines are: Heat stability, no cold chain of refrigerators; affordable; zero risk of cross infection; individual injection devices and vaccine doses packaged together; simple and easy to use; easy and safe disposal; no wastage; minimal discomfort; and minimum volume.

It is known to package parenteral medications in disposable, single dose delivery devices. On approach is to package single doses of vaccines in simple plastic blisters or collapsible tubes with an integral hypodermic needle attached. Examples are disclosed in U.S. Pat. Nos. 4,013, 073 to Cunningham and 4,018,222 to McAleer et al. The Uniject™ plastic blister device (Becton Dickinson and Co.) is another example. Known single-use injectors require medical expertise to use and are intimidating because of the naked needle.

Some single-use injectors are designed to self-destruct, eliminating the temptation to re-use. Examples are disclosed in U.S. Pat. Nos. 3,998,224 to Chiquiar-Arias, 4,233,975 to Yerman, and 4,391,272 to Staempfli. Another example is the Soloshot™ syringe (manufactured by Becton Dickinson). These syringes are more expensive than standard syringes, and also require medical expertise to use.

The use of breakable tabs and snap rings in plastic containers, such as bottles, is well known. These devices are commonly used for tamper protection, sealing, and the like. An early example is disclosed in U.S. Pat. No. 3,407,956 to Linkletter, which shows a removable and replaceable bottle cap. The plastic cap has an annular beaded molded on the inside, which overrides a similar bead molded on the outside of the neck of the bottle. Natural elasticity of the materials used in manufacturing the cap permit it to expand temporarily. This allows the beads to override and then to contract again immediately once the beads have passed each other. This seats the cap firmly on the container and provides a good seal.

Needleless injectors are well known. These injectors use a fine stream of pressurized liquid to penetrate the skin. The pain is considerably less than that experienced during a conventional injection. Early designs used high pressure throughout the injection. Later, it was realized that high pressure was required only at the start of the injection, to punch a hole through the tough epidermis. The bulk of the injection could then be infused along the initial track under much lower pressure. U.S. Pat. No. 2,704,542 to Scherer and 3,908,651 to Fudge disclose examples of this design. The engineering demands of changing the pressure during the injection and resulting complexity have limited the use of such injectors.

Standard high-pressure needleless jet injectors are also inherently complex, requiring precision engineering with dozens of machined steel parts. Most designs have focused on the production of robust, reliable, heavy-duty machines capable of many injections at high rates for mass immunization campaigns. Infection due to cross-contamination in such jet injectors has been reported. This may be due to the high pressures caused in the tissues. As the distended tissue relaxes and the pressure simultaneously falls in the injector, liquid can be sucked into the injector. This liquid may be contaminated with blood or interstitial fluid. This problem has been addressed by the development of single-use vials which insert into the jet injector. This approach may be combined with a replaceable nozzle and a vaccine fluid path of cheap plastic, as disclosed in U.S. Pat. 4,266,541 to Landau.

A mono-dose disposable jet injector has been developed under the trademark "Intraject" by Weston Medical, UK. Similar to other jet injectors, this injector uses a highly compressed gas in a canister to propel the vaccine dose. See Lloyd J. S., Aguado M. T., Pre-Filled Monodose Injection Devices: A safety standard for new vaccines, or a revolution in the delivery of immunizations?, Global Programme on Vaccines and Immunization, World Health Organization, May 1998.

It is known that extraordinary stability can be conferred on very labile biomolecules by drying them in glasses formed from certain sugars. Trehalose is one example. See U.S. Pat. No. 4,891,319 to Roser, and Colaco C., Sen S., Thangavelu M., Pinder S., and Roser, B. J., Extraordinary stability of enzymes dried in trehalose: Simplified molecular biology. *Biotechnol.* 10 1007–1011 (1992). A similar technique can be applied to stabilized vaccines. See Gribbon E. M., Sen S., Roser B. J. and Kampinga J., Stabilisation of Vaccines Using Trehalose (Q-T4) Technology, in F. Brown, (ed) New Approaches to Stabilisation of Vaccine Potency *Dev Biol Stand* Basel Karger 87 193–199 (1996).

A more recent development in glass-forming preparations using sugar derivatives is stabilization brought about by the active biomolecules remaining in solid solution in the "solid solvent" phase of the glass matrix. The biomolecules are stable because of the extremely high viscosity of the inert glass. Molecular diffusion and molecular motion are negligible in these solid solutions. Chemical reactions, which depend on the reactive species being free to diffuse together, are therefore non-existent. Providing the glass itself is chemically non-reactive and dry, the product typically remains stable at temperatures up to the softening point of the glass. This is often expressed as the "glass-transition temperature" or Tg. Only as the glass begins to soften and melt can molecular diffusion and hence degradation start.. Even at temperatures above the Tg, it takes a certain time for damage to occur and the rate of deterioration is slow because the viscosity of even the softened glass is high. Because degradation reactions are chemical processes with typical kinetics, the determining factor in product damage is actually a mathematical product of the elevated temperature and the time of exposure rather than just the high temperature. Even fragile compounds in these glasses can be briefly exposed to high temperatures with insignificant damage. While sugar glasses have advantages in stability over conventional parenteral preparations, the other difficulties of conventional parenteral injection remain, such as dose mismeasurement, pain, and infection risk.

Phosphate glasses are also suitable for stabilization of parenteral medications. See U.S. Pat. No. 4,698,318 to Vogel et al. Phosphate glasses are typically much stronger than sugar glasses. Because of their strength, phosphate glasses are often used as structural elements in bone repair. Mixtures of metal carboxylates such as the acetate salts of sodium, potassium, calcium and zinc also form excellent glasses, PCT Publication No WO90/11756). By using different mixtures of the individual carboxylates and by using different metal cations, it is possible to tailor these phosphate and carboxylate glasses to dissolve at different, specific rates in body fluids. Being composed of simple chemicals normally prevalent in the body, phosphate and carboxylate glasses exhibit very low toxicity. The major disadvantage of these glasses is the high temperature needed to melt them. This precluded most drugs being incorporated in the glass in solid solution, and restricted their use to pre-formed hollow tubes which were loaded with stable powdered drugs. See U.S. Pat. Nos. 4,793,997 and 4,866,097 to Drake et al. Because it is difficult to fill narrow tubes with dry powders, phosphate glass tubes are generally of large diameter. Large diameter tubes are traumatic to inject and suitable only for veterinary applications.

One approach to the problem of filling narrow tubes with powdered actives is to suspend the powdered drug or vaccine in a non-aqueous liquid in which it is insoluble. These suspensions flow more readily into fine capillary tubes and carry the powdered active with them. Many organic solvents such as ethanol, acetone, dichloromethane, chloroform, and toluene etc. may be used. However, many of these industrial solvents can react destructively with biological molecules. This difficulty can be avoided by first enclosing the actives in stabilizing sugar glasses, as disclosed in U.S. Pat. No. 5,589,167 to Cleland et al. and in Gnbbon E., Hatley R, Gard T., Blair J., Kampinga J. and Roser B. Q-T4 Stabilisation and novel drug delivery formats, *Conf. Report Amer. Assoc. Pharm. Soc.,* 10th annual meeting, Miami Beach, Fla. (1995),

BRIEF SUMMARY OF THE INVENTION

The present invention is a single use injector device for injecting parenteral medications which operates by hand force. The injector device has a plunger section and a base. As hand force is applied to a moving portion of the plunger section, a snap means such as break tabs or a snap ring resists its motion toward the patient's skin surface. The snap means releases abruptly as the hand force reaches a snap point. The motion of the moving portion then drives the medication through the skin surface and into the body of the patient. If the medication is in liquid form, the actual injection may be carried out through a hollow needle attached to the plunger section. Alternatively, the suddenly increased pressure of the medication at the snap point may be used to form a liquid jet for needleless injection. Part or all of the medication may be contained in a glass needle which dissolves in the body after injection. The injector device requires little training to use, reduces perceived pain, and improves injection safety.

BRIEF DESCRIPTION OF THE DRAWINGS

FIGS. 2A, 2B, and 2C are cross-sectional views of the injector device of FIG. 1, showing in succession the penetration of the skin by the needle, the injection of the liquid medication, and needle withdrawal.

FIGS. 3A, 3B, and 3C are cross-sectional views of an injector device having a shaft for injection of a glass needle, and show in succession the initial position, the injection of the glass needle, and the withdrawal of the shaft.

FIGS. 4A and 4B are cross-sectional views of an injector device having a tubular shaft for injection of a glass needle along with liquid medication, showing in succession the initial position and the withdrawal of the shaft after the liquid medication is injected along the glass needle track.

FIGS. 6A, 6B, and 6C are cross-sectional views of an injector device having jet injection means, showing in succession the breaking of the break tabs, the formation of the liquid jet, and the completed injection.

FIGS. 7A and 7B are cross-sectional views of an injector device having a snap ring and jet injection, showing in succession the initial position and the completed injection.

FIGS. 9A, 9B, 9C, and 9D are cross-sectional views of an injector device in which the hand force is applied directly to the plunger, having a hollow needle for injection of liquid medication, and showing in succession the initial position, penetration of the hollow needle, injection of the medication, and withdrawal of the needle.

FIGS. 10A, 10B, 10C, and 10D are cross-sectional views of an injector device in which the hand force is applied directly to the plunger, having a shaft for injection of a glass needle, and showing in succession the packaged injector device, the initial position, the injection of the glass needle, and withdrawal of the shaft.

DESCRIPTION OF PREFERRED EMBODIMENTS

Figure 1:
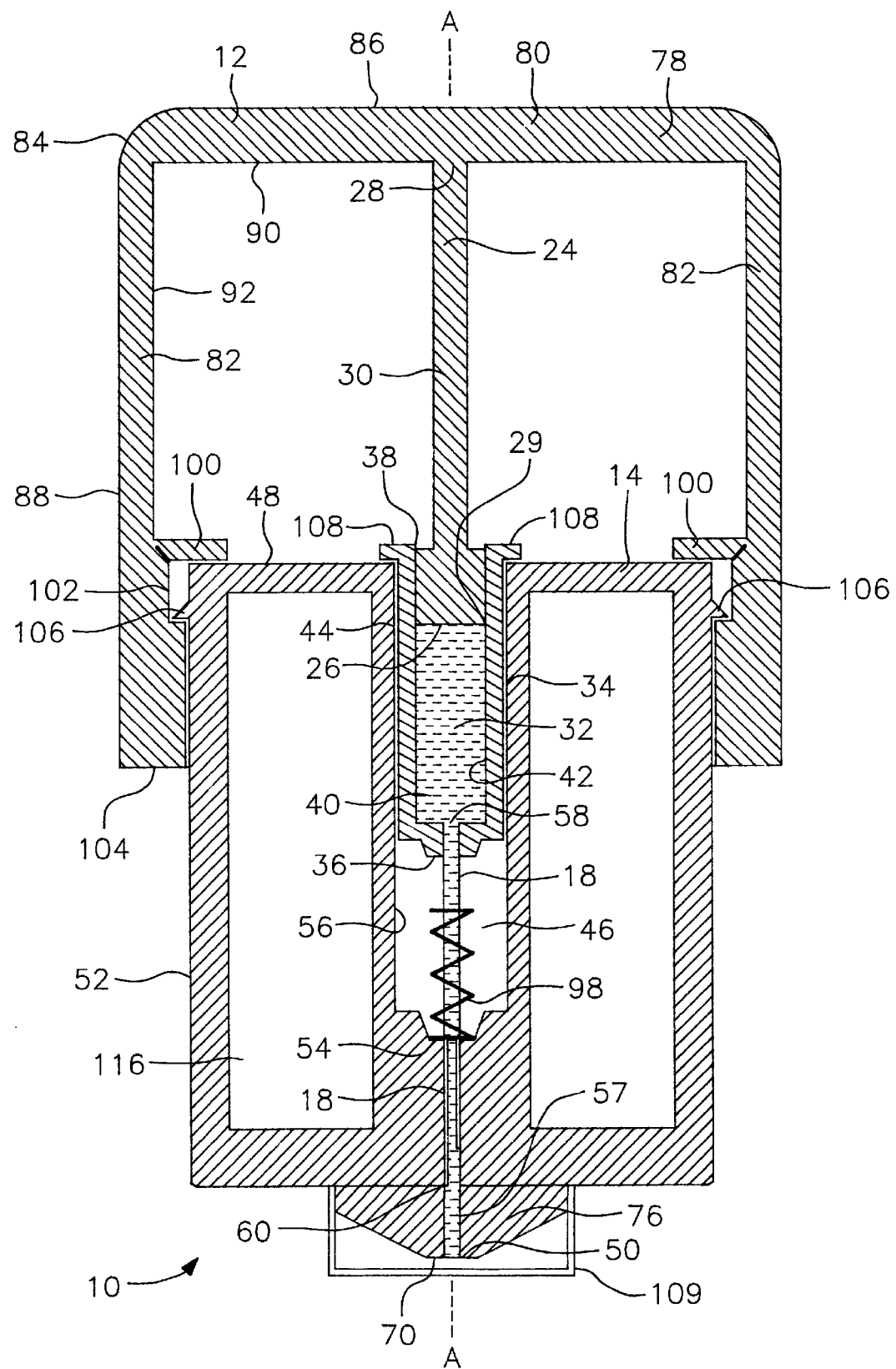
FIG. 1 is a cross-sectional view of an injector device in the initial position, taken parallel to the longitudinal axis, the device having break tabs, a needle, and a barrel containing liquid medication.

The present invention is a single use injector device 10 for injecting parenteral medications into the body of a patient. The injector device operates by hand force, without requiring any other force to complete the injection. The injector device 10 has a plunger section 12 and a base 14. As hand force is applied to a moving portion of the plunger section, a snap means such as break tabs or a snap ring resists its motion toward the patient's skin surface 16. See FIGS. 1 and 2. The snap means releases abruptly as the hand force reaches a snap point. The same motion of the moving portion then drives the medication through the skin surface 16 and into the body of the patient.

A variety of injection means may be used for the actual injection of the medication. If the medication is in liquid form, the injection may be carried out through a hollow needle 18 attached to the plunger section 12. Alternatively, the suddenly increased pressure of the medication at the snap point may be used to form a liquid jet 20 for needleless injection, as in FIG. 6B. Part or all of the medication may be contained in a glass needle 22 which dissolves in the body after injection, as in FIG. 3C.

Figure 8:
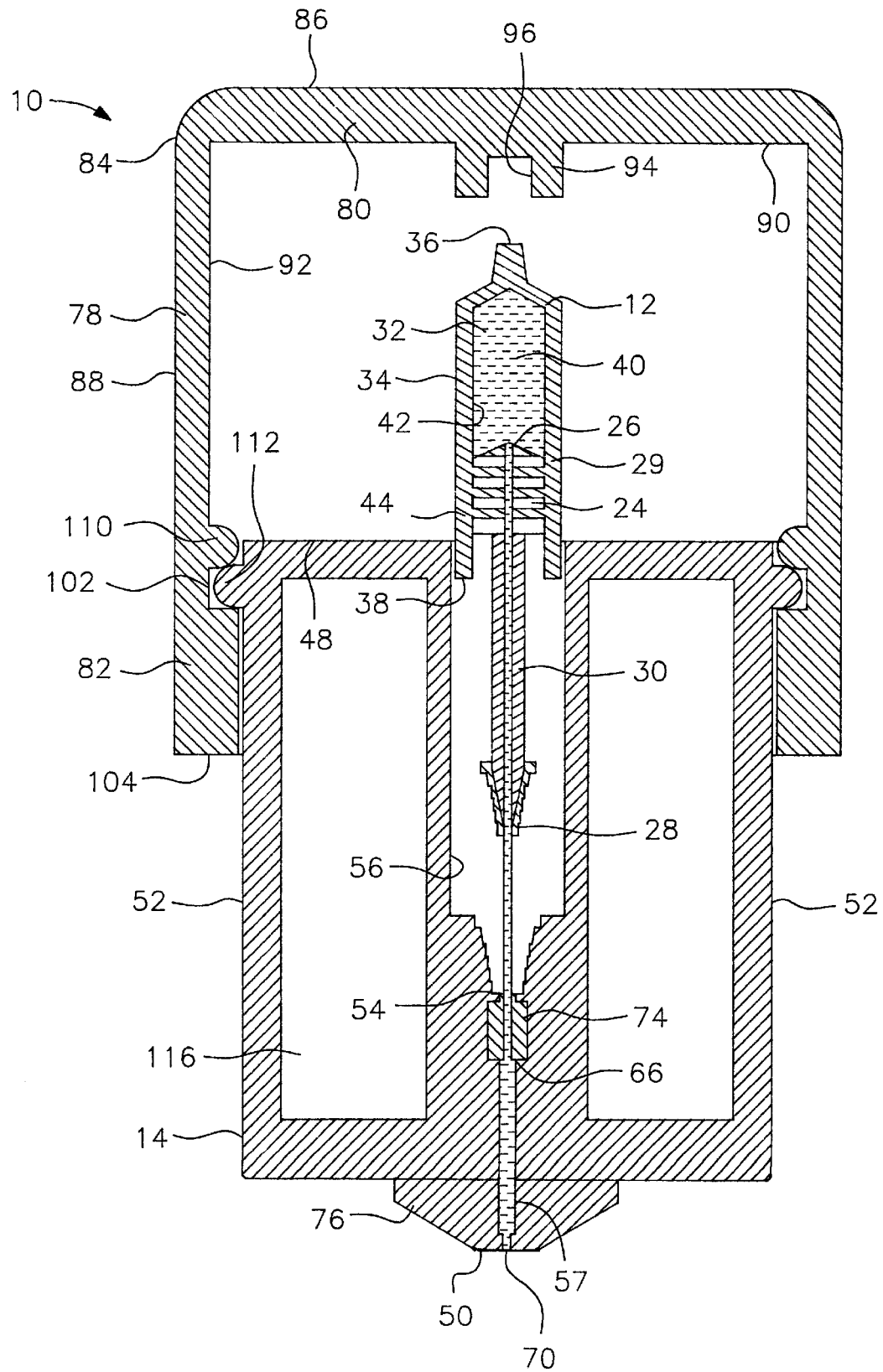
FIG. 8 is a cross-sectional view of an injector device in the initial position, having a barrel between the cap and the plunger.
Figure 11A:
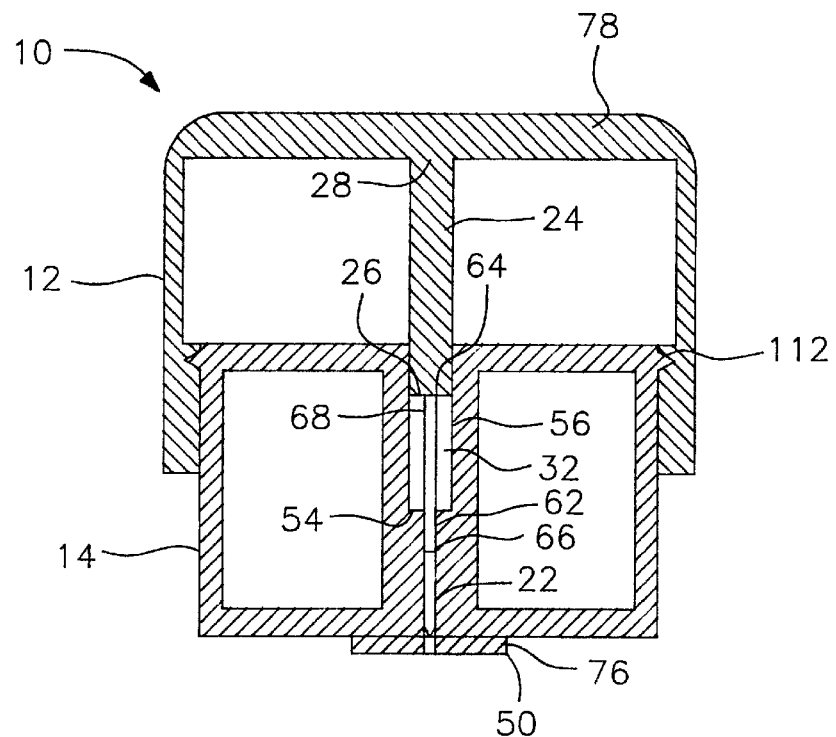
FIGS. 11A and 11B are cross-sectional views of an injector device having a tubular shaft for injection of a glass needle, the tubular shaft having perforations for injection of liquid medication from the cavity.
Figure 11B:
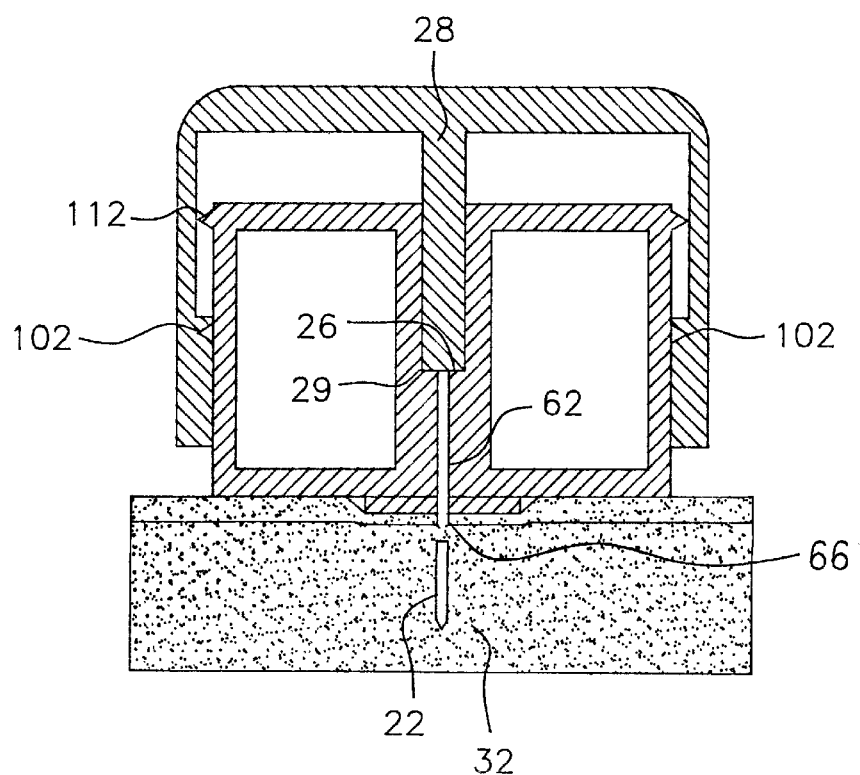

The plunger section 12 includes a plunger 24. The plunger section is at least partially composed of plastic, preferably completely composed of plastic. The plunger 24 has a longitudinal axis A, as shown in FIG. 1. The plunger 24 also has a first end 26 and a second end 28. The first end has a periphery 29. The plunger preferably has a circular cross-section (taken perpendicular to the longitudinal axis). The plunger may have a uniform diameter from the first end 26 to the second end 28, as shown in FIGS. 11A and 11B. To save weight and materials, the plunger may have a central section 30 which is narrower than the first end 26, as shown in FIGS. 1 and 8. The central section 30 may be narrower than either the first end 26 or the second end 28, as in FIG. 9A. When at least a part of the parenteral medication is a liquid medication 32 contained in a reservoir means, the first end 26 of the plunger is the end which contacts the medication in the reservoir means.

The plunger section 12 may include a barrel 34, as shown in FIGS. 1–2C and 4A–9D. The barrel 34 is tubular and preferably has a circular cross-section. The barrel has a first end 36 and a second end 38. The first end 36 is at least partially closed, so that the barrel is cup-shaped. The barrel 34 has a reservoir 40 adapted to contain the liquid medication 32. The longitudinal axis of the barrel is coincident with the longitudinal axis of the plunger 24. The barrel has an inner surface 42 and an outer surface 44. The barrel 34 is located at least partially within the cavity 46 of the base 14. The shape of the barrel in cross section corresponds to the shape of the plunger, so that a snug sliding fit is produced. The barrel 34 slides with respect to the cavity 46, parallel to the longitudinal axis of the cavity.

If the injector device includes a barrel 34, the first end 26 of the plunger is located within the barrel, both in the initial position and during the injection. The first end 26 contacts the liquid medication 32. The periphery 29 of the first end 26 of the plunger forms a liquid-tight, sliding seal with the inner surface 42 of the barrel. The plunger 24 slides with respect to the barrel 34 parallel to the longitudinal axis of the plunger. The motion of the moving portion of the plunger section 12 toward the skin surface 16 after the snap point is reached expels the liquid medication from the reservoir 40 and injects the liquid medication 32 into the body of the patient. The sliding barrel allows the injection of a liquid medication to be carefully controlled in stages, and helps to make injections easy to do correctly, even for a minimally trained health worker.

The injector device contains a single dose of the liquid medication, such as a drug or a vaccine. The liquid medication may be a stable form, so that refrigeration is not required. If the liquid medication is unstable, the injector devices can be refrigerated. The injector device 10 can be pre-filled with sterile formulations of a very wide range of active solutions and suspensions. The injector device is ideally suited to bulk manufacture, distribution and delivery of vaccines and drugs for human and veterinary use.

The base 14 is generally tubular and has a plunger end 48, a nozzle end 50, and an outer surface 52. The base is at least partially composed of plastic, and preferably entirely composed of plastic. The plastic is preferably opaque or translucent, particularly if any injection means involving a needle is used. The base and plunger section can be easily constructed using inexpensive plastic injection molding technology, making the injector device sufficiently cheap to be disposable. The plastic may be sterilizable by heat, radiation, or chemicals.

The cavity 46 of the base has a nozzle end 54 and a cavity surface 56. The longitudinal axis of the cavity 46 is coincident with the longitudinal axis of the plunger. The plunger 24 is located at least partially within the cavity. The plunger slides within the cavity parallel to the longitudinal axis of the cavity. If a barrel is used, the barrel is located between the plunger 24 and the cavity surface 56. Preferably the base includes a bore 57, of smaller diameter than the cavity, extending between the nozzle end 54 of the cavity and the nozzle end 50 of the base.

The injector device has snap means for resisting movement of at least a moving portion of the plunger section from an initial position toward the skin surface as the hand force is applied to the moving portion. Preferably the entire plunger section is the moving portion. The snap means releases the moving portion of the plunger section abruptly as the snap point is reached. After the snap point is reached the moving portion of the plunger section moves rapidly toward the skin surface. Typically the snap point is reached when the hand force is 2N–100 N, preferably 10–40 N, most preferably 20–30 N. A breaking force significantly smaller than this may not complete the injection rapidly enough for optimum patient comfort; a larger force may be difficult for a health worker to exert.

The plunger section remains essentially stationary up to the snap point, since the snap means holds it back. At the snap point the hand force is automatically and abruptly switched from overcoming the snap means to accelerating the moving portion of the plunger section. The plunger section is light in weight, typically only a few grams, and resistance to the motion is small. A very rapid acceleration therefore results. The injection occurs within a very short space of time after the snap point, typically a fraction of a second.

The snap means differs from previous use of springs to provide power for an injection, as in EP0595508 to Alchas et al. Such a spring does not initially resist hand pressure, and then suddenly snap. The snap means of the present invention does not require a trigger to release it; rather it releases automatically as the breaking strength of a break tab is reached, or as the limit of elastic deformation is reached for a snap ring. A continuous motion of the hand both snaps the snap means and completes the injection. The snap means does not include a spring. Springs may be used in the injector device as part of mechanisms other than the snap means, such as for withdrawal of a needle.

If a barrel 34 is used, the moving portion of the plunger section includes the plunger 24 and the barrel. Their motion may not be exactly simultaneous; either the plunger or the barrel may move first after the snap point. The barrel may be oriented with the first end 36 up (further from the skin surface), as in FIG. 8, or with the first end down (closer to the skin surface), as in FIGS. 1 and 5. In the "first end down" configuration, the first end 36 of the barrel is located between the first end 26 of the plunger and the nozzle end 54 of the cavity. In the "first end up" configuration, the plunger 24 is located between the first end 36 of the barrel and the nozzle end 54 of the cavity.

If no barrel is used, the moving portion of the plunger section includes the plunger. In this case the first end 26 of the plunger is located within the cavity 46. The periphery 29 of the first end of the plunger contacts the cavity surface 56, instead of the inner surface of the barrel 42.

Several different injection means for injecting the medication are suited for use with the injector device. The various injection mechanisms have in common that the abrupt motion of the moving portion of the plunger section toward the skin surface after the snap point is reached drives the medication through the skin surface and into the body of the patient. Somewhat different injection means are required for injecting liquid medications, solid medications (such as glass needles), and combinations of liquid and solid medications.

If at least a part of the parenteral medication is a liquid medication, the injector device 10 may include a reservoir means for containing the liquid medication. The reservoir means may be the reservoir 40 if a barrel is used, or the cavity 46 if no barrel is used. Preferably the device is pre-loaded with sterile liquid in the factory. The liquid medication can be a conventional liquid formulation of a drug or vaccine, which would require that the device be refrigerated. Preferably a stable non-aqueous ready-to-inject liquid suspension is used, as described in PCT application WO98/41188 and U.S. patent application Ser. No. 09/271, 204, so that no refrigeration is required.

A hollow needle 18 may be part of the injection means, as shown diagrammatically in FIGS. 1, 2A–2C, and 9A–9D. The hollow needle is preferably made of steel, and is a sliding fit in the bore 57. The hollow needle is tubular and has an attachment end 58 and a free end 60. The attachment end 58 is attached to the plunger section 12. The free end 60 is sharp, in the conventional manner. The interior space of the hollow needle is in fluid communication with the reservoir means. The attachment end may be open, as shown in FIG. 1, or the hollow needle may have a perforation near the attachment end for entry of the liquid medication. If a barrel is used in "first end down" configuration, the attachment end of the needle preferably attaches to the first end 36 of the barrel, as in FIGS. 1 and 9A–9D. If a barrel is used in "first end up" configuration, as in FIG. 8, the attachment end of the needle preferably attaches to the second end 28 of the plunger.

The free end 60 of the hollow needle is located within the bore 57 when the plunger section is in the initial position. The motion of the moving portion of the plunger section after the snap point is reached drives the free end 60 of the hollow needle through the skin surface 16. The same motion expels the liquid medication from the reservoir means through the hollow needle into the body of the patient. The needle is driven to a preset depth in the subcutaneous tissue or muscle. Preferably a withdrawal mechanism, such as a gas spring or a coil spring, is included to automatically withdraw the free end of the hollow needle back within the bore as soon as the injection is complete. A sealing membrane 70 may cover the nozzle end 50 of the base. The sizes of needles, volume of injected liquid, and other dimensions and materials in the construction of the injector device 10 are variable, without undue experimentation.

The combination of the hollow needle 18 with the injector device has several advantages over conventional syringes. The injector device 10 acts as a storage container and a ready-to-inject delivery device. The needle is hidden within the bore, so the patient does not see it at all before the injection. If a withdrawal mechanism is included, the patient never sees the needle. This in itself significantly reduces the anxiety and therefore the pain experienced in injections. The injection occurs very quickly, within a fraction of a second, which also reduces pain. The injector device requires virtually no training to operate, and delivers its injection to a factory-set depth. A short needle can be used, since the needle does not have to be handled by a health care worker. The injector device is suitable for the delivery of most parenteral drugs and vaccines in animals and humans.

The combination of the conventional hollow needle with a snap means is a significant improvement over prior art disposable injectors. A conventional syringe has a plunger within a base. The interior of the base in a conventional disposable syringe often has a projecting ring. However, the projecting ring has a completely different function in resisting the withdrawal of the plunger from the base. Nothing impedes the motion of the plunger toward the skin surface other than the medication's resistance to flow through the needle. A highly skilled health worker may be able to produce a rapid acceleration on the plunger in a conventional syringe simultaneously with a rapid penetration of the needle into the skin. This leads to a relatively comfortable, rapid injection. However, typical health workers achieve a much slower penetration, and inject the medication relatively slowly after penetration. This slow injection process makes the injection much more painful. The snap means of the injector device allows a relatively untrained health worker to achieve very rapid injections, even more rapid than a highly skilled worker.

Conventional self-destruct syringes also frequently have various projections or rings to prevent the plunger from being pulled out once the injection has been made. See U.S. Pat. No. 4,39,272 to Staempfli. However, these are not equivalent to the snap means of the present invention. They operate after the injection is made, and the motion involved does not operate to inject the medication. U.S. Pat. No. 4,233,975 to Yerman, for example, has members which lock together after the injection is made to prevent later intake or outflow through the needle.

The injector device 10 of the present invention is inexpensive to manufacture and is therefore ideal as a disposable single dose device. The plunger section, barrel, needle, etc. can be custom manufactured along with the cap and base. However, an existing syringe with an integral needle can be used as part of the injector device if desired. For example, such a syringe might be modified by the provision of a snap ring within a cap. A pre-filled syringe can be used for such modifications, reducing manufacturing costs.

Another injection means suitable for the injector device 10 includes a glass needle. Several configurations are suitable for use with the injector device 10. A preferred configuration is shown in FIGS. 4A, 4B, and 10A–10D. The plunger section 12 includes a shaft 62. The shaft is preferably cylindrical, with a circular cross-section. The diameter is preferably about the same as the diameter of the glass needle, or only slightly larger; a shaft with too large a diameter may not easily follow the needle track 63 through the skin. A diameter of 1 mm is suitable. The shaft 62 has an attachment end 64 and a free end 66. The attachment end 64 may attach to the barrel, as in FIGS. 4A–4B, or to the first end 26 of the plunger, as in FIGS. 10A–10D. The axis of the shaft 62 extends coincident with the longitudinal axis of the plunger and extends toward the skin surface relative to the remainder of the plunger section. The free end 66 of the shaft is blunt. The free end of the shaft is located within the bore 57 when the plunger section 12 is in the initial position.

The glass needle 22 preferably is adapted to contain at least a part of the parenteral medication. Preferably the glass needle is composed at least partially of a glass such as sugar glass, trehalose glass, trehalose octaacetate glass, glucose pentaacetate glass, silica glass, sodium phosphate glass, phosphate glass, metal carboxylate glass, Palatinit glass, and mannitol glass. The fiber pulling method may be used to make needles from melts. The glass needle may be solid, with the parenteral medication incorporated into the glass. Mixtures of glasses may also be used; for example, needles composed of mixtures of the hydrophobically modified sugars trehalose octaacetate and glucose pentaacetate have been prepared. Alternatively, the glass needle may be tubular with sealed ends, with part or all of the parenteral medication contained in the interior.

Glass needles are physically stable as glasses when stored in snap-cap plastic vials under ambient room conditions for over 1 year. The sugar glasses and the hydrophobically modified carbohydrate glasses are inherently very brittle. In contrast, the phosphate glass needles are physically strong. Trehalose glass needles can be strengthened by adding up to 10% w/w of a water-soluble polymer such as polyvinylpyrollidone (Kollidon 30) before melting.

By using modified, slowly-dissolving glass forming materials the rate of solution of the needle material in body fluids can be regulated. Delayed or controlled release of the actives in such needles can therefore be achieved. This is particularly useful when successive doses are required, as is the case for many vaccines to achieve full immunity. This technology can be used to provide a complete course of vaccination in a single injection.

EXAMPLE 1

Perfluorocarbon (PFC) fluid may hold two separate stabilized medications in suspension: (1) an immediately soluble medication stabilized by glass microspheres of sugar derivatives or the like, providing the priming dose of antigens; (2) a slow or delayed release formulation based on either slowly dissolving hydrophobic glasses or biodegradable polymers such as the polylactide/glycolide plastics. This provides the first booster dose of vaccine as it releases its actives over the following weeks. See Johansen P, Merkle H P, and Gander B, Improved tetanus toxoid release and efficacy from PLGA microspheres by co-encapsulating albumin, Proc Controlled Release Soc 25, 633–634 (1998a). Finally, the hollow glass needle itself is formulated from a slowly dissolving mixed phosphate or carboxylate glass which takes several months for the glass wall to breach. If this needle is filled with soluble glass microspheres of the vaccine, this will be released at the appropriate time to provide the final booster dose of the vaccination protocol. The suspensions in PFC liquids are indefinitely stable, so that they are ideally suited to packaging in a single use injector device.

EXAMPLE 2

A controlled-release needle was made from microsphere powder of trehalose glass, containing the dye mordant blue 9 (MB9). The powder was spray dried and stirred into a melt of the slowly-soluble sugar derivative, trehalose octaacetate (TOAC) at a ratio of 10% w/w. The mixture was loaded into a pre heated syringe. A rod was extruded onto a sinless steel plate and cooled. This composite needle was examined microscopically and found to have the dark blue microspheres of the trehalose glass evenly dispersed throughout the clear, colorless TOAC rod. This confirmed that the trehalose microspheres remained solid and glassy in the melt and that this intensely hydrophilic glass formed a stable monodisperse suspension throughout the hydrophobic TOAC melt.

The relatively low force necessary to drive a sharp glass needle through the epidermis achieves a low resistance hole through the epidermis and into the loose subcutaneous connective tissues. The needle leaves a perforated track 63 of tissue damage along which liquid can flow under low pressure. The sharp glass needle is of similar dimensions to conventional needles. Since the injection of a glass needle does not require very precise tolerances, manufacturing costs are relatively low.

For example, a simple, low cost injector device may be produced with a single drug in suspension in PFC fluid. This drug may be delivered through the tissues along the needle track formed by an injected solid glass needle of soluble phosphates, metal carboxylates or sugar. The water-soluble needle acts simply as a "pioneer" projectile, which produces the low-resistance pathway through the tissue along which the liquid suspension can flow. This simple injector with no needle visible either before or after injection is perceived by the patient as essentially pain free. Patient compliance is significantly increased.

EXAMPLE 3

The open end of precision glass capillary tubes in various internal diameters from 140 to 600 $\mu$m (Dade acupette, Camlab DMP 025, Blaubrand Intramark or Denley Instruments Bilby capillaries) were immersed in a 20% w/v stable PFC suspension of sugar glass microspheres. Gentle suction was applied via a capillary tube filling device (Blaubrand Intramark). In all cases the suspension flowed easily and evenly into the capillary.

The glass needle 22 is preferably located within the bore 57 and between the shaft 62 and the nozzle end 50 of the base when the plunger section is in the initial position. A sealing membrane 70 may be used to cover the nozzle end 50 of the base and retain the glass needle in the initial position. The motion of the moving portion of the plunger section after the snap point is reached drives the shaft 62 toward the skin surface 16 through the bore 57. The free end 66 of the shaft strikes the glass needle and drives it through the skin surface. The glass needle 22 then remains in the body of the patient and dissolves there, releasing the medication. The glass needle cannot be seen by the patient, either before or after the injection.

The shaft 62 maybe solid, as shown in FIGS. 10A–10D. A solid shaft is relatively inexpensive to manufacture as an integral part of the plunger.

The shaft 62 may be tubular, as shown in FIGS. 4A–4B. A tubular shaft or cannula attached to a barrel may be open at the attachment end 64 and in fluid communication with the reservoir. A tubular shaft 62 allows for the injection of both the glass needle and a liquid medication. The liquid medication is contained in a reservoir means, such as the reservoir of the barrel or a liquid-tight cavity. The interior of the shaft 62 is in fluid communication with the reservoir means. The motion of the moving portion of the plunger section after the snap point is reached drives the free end of the shaft through the skin surface after the glass needle 22. The liquid medication 32 is expelled from the reservoir means through the shaft 62 and into the body of the patient after the glass needle. See FIGS. 4A and 4B.

An alternative injection means including a glass needle is shown in FIGS. 11A and 11B. At least a part of the liquid medication is contained in the cavity when the plunger section is in the initial position. The shaft 62 has one or more perforations 68 near the attachment end, through which the interior of the shaft is in fluid communication with the cavity. See FIG. 11A. After the glass needle penetrates the skin, the liquid medication is expelled from the cavity through the perforation 68 and into the body of the patient after the glass needle.

Another design for injection of a glass needle 22 is shown in FIGS. 3A–3C. The first end 26 of the plunger 24 is narrow, having a diameter about the same as or only slightly larger than the glass needle 22. The cavity 46 extends from the plunger end 48 of the base to the nozzle end 50 of the base. The first end 26 of the plunger is blunt, and is located within the cavity when the plunger section 12 is in the initial position. The cavity has a narrow diameter, such as about 1 mm. The plunger is a snug sliding fit within the cavity. The glass needle 22 is located within the cavity 46 and between the first end 26 of the plunger and the nozzle end 50 of the base when the plunger section is in the initial position. The motion of the moving portion of the plunger section after the snap point is reached drives the first end 26 of the plunger toward the skin surface through the cavity. The first end of the plunger strikes the glass needle and drives it through the skin surface. Preferably the plunger 24 has a stop-collar 69 at the second end 28, with a larger diameter than the cavity. This stops the plunger at the factory pre-set distance, preventing it from penetrating too deeply into the skin.

The injector device shown in FIGS. 10A–10D contains no free liquid. The manufacturing tolerances for this device are therefore less stringent, since liquid-tight seals are not required. This reduces manufacturing costs.

EXAMPLE 4

A prototype injector device of the type depicted in FIGS. 10A–10D was machined from nylon. The plunger was made from ground stainless steel rod 1 mm in diameter. The firing mechanism consisted of snap rings as in U.S. Pat. No. 3,407,956, incorporated by reference. Firing pressure was adjusted by stepwise reduction of the diameter of the snap ring to about 30 N of force (equivalent to a weight of about 3 Kg), using a top pan balance for calibration. This is a force which can be easily produced by even a frail person, and is similar to the force required to replace the cap on a conventional snap-cap tablet container. Glass needles one cm long were made from precision silica glass capillary tubing 1 mm in diameter (Dade Acupette disposable 10 $\mu$l capillary pipettes P4518-10). Sharp points were fashioned by heating and pulling. The gun was fired several times into a fresh loin of pork, which had been equilibrated at 37° C. overnight to bring the subcutaneous fat and other tissues to the correct consistency. The location of the needles was subsequently found by sharp dissection. In every case the needles were found in the deep subcutaneous connective tissue. A needle was also fired into the deltoid muscle of a human volunteer. Apart from a slight ache, which disappeared within one minute after injection, the volunteer reported that the injection was comfortable. A small single bead of a few microliters of blood appeared at the injection site. There were no other sequelae.

Another injection means particularly suited for use with the injector device 10 is jet injection. See FIGS. 5, 6A–6C, 7A–7B, and 8. Jet injection requires that at least a part of the parenteral medication is a liquid medication. The liquid medication is contained in the reservoir means (the cavity, reservoir, or the like) and in the bore. The bore may have a diameter of about 1 mm. The bore is in fluid communication with the reservoir means. The end of the bore is sealed by a sealing membrane 70 or the like at the nozzle end 50 of the base. The liquid medication is used to form a liquid jet 20, as in FIG. 6B. The motion of the moving portion of the plunger section after the snap point is reached increases the pressure of the liquid medication 32 within the reservoir means and the bore. The continuity of the liquid provides a ram effect, since the liquid is essentially incompressible. The snap means allows for a nearly instantaneous increase to a sufficiently high pressure to form a liquid jet 20. The entire force of about 30 N applied to the plunger section is transmitted to the tiny area of skin underlying the nozzle end of the bore. The liquid jet 20 pierces the skin. The remainder of the liquid medication is expelled from the reservoir means through the bore 57 and into the body of the patient along the track through the skin formed by the liquid jet. The patient feels only a sensation of pressure against the skin.

Use of the injector device 10 allows jet injection of a liquid medication without any need for the complex systems required by prior art needleless devices. The discovery that a force easily generated by the human hand alone is sufficient to power jet injection is truly remarkable. As the liquid jet must be of very narrow diameter, relatively precise manufacturing tolerances are required, particularly in the nozzle end of the base. However, the benefits of liquid jet injection can be obtained without the complex engineering needed when high pressure is supplied by compressed air, heavy springs, a vacuum source, or similar means known in the prior art.

Several designs are possible for the jet injection means. The plunger section may include a tubular shaft 62, as in FIG. 5. The shaft has an attachment end 64 and a free end 66. The shaft axis is coincident with the longitudinal axis of the plunger and toward the skin surface relative to the plunger section. The free end 66 of the shaft is located within the bore when the plunger section is in the initial position. The nozzle end 72 of the bore is sealed by the sealing membrane 70. The bore includes a liquid- and pressure-tight seal 74 surrounding the shaft 62, to assure that the liquid remains contained and the liquid jet is directed toward the skin. The seal may be produced by a tight fit with the shaft, or by a section of elastomeric tubing such as silicone, neoprene or butyl rubber around the shaft. The tapered nozzle 76 at the nozzle end 50 of the base is preferably integral with the remainder of the base, and is engineered to focus the liquid jet and place it in the right position for piercing the skin.

EXAMPLE 5

Figure 5:
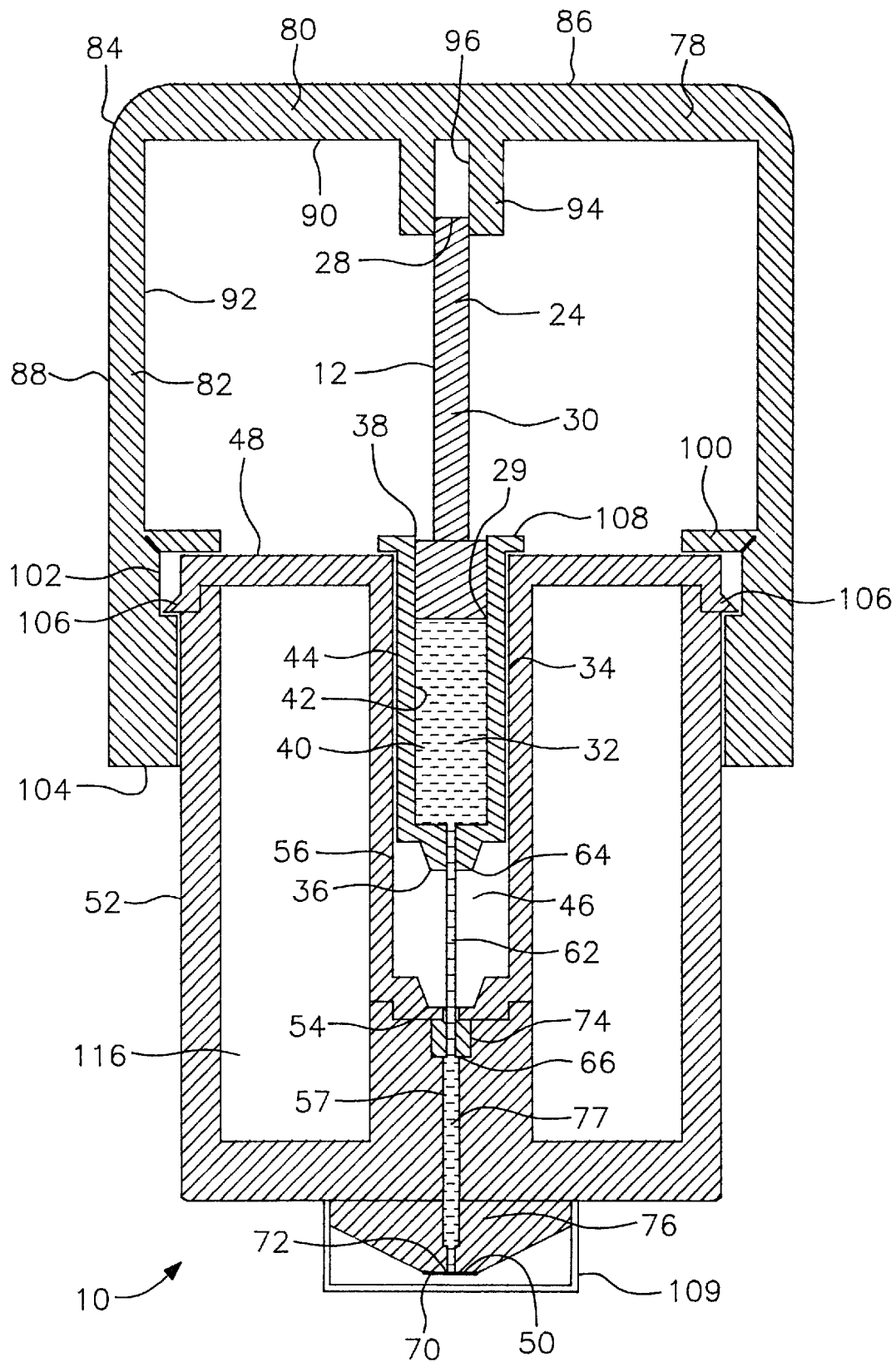
FIG. 5 is a cross-sectional view of an injector device in the initial position, the injector device having jet injection and a plunger which is struck by a cap after the snap point is reached.

For the injector device 10 as shown in FIG. 5, the diameter of the bore 57 is about 0.6 mm (the size of the standard 23 gauge vaccination needle). The instantaneous pressure exerted on the epidermis beneath the nozzle end of the bore is about 106 N/mm$^2$, more than 100 Mega Pascals (MPa) or over 15,000 psi. This compares with the usual range of pressure in commercial liquid jet injectors of about 3,000–6,000 psi (roughly 20–40 MPa). This pressure is exerted while the small volume of liquid is displaced by the travel of the shaft down the high-pressure portion 77 of the bore until the barrel reaches the nozzle end of the cavity. This liquid volume is about 3 μl. Under this pressure, it punches a hole through the epidermis and into the loose subcutaneous tissue. The time required is a small fraction of a second. The plunger continues to move, driving the remaining liquid along the same track. For a 5 mm diameter plunger, the secondary pressure is about 1.5 MPa, which is adequate to deliver the remainder of the dose. The size of the hole punched in the skin is determined by the diameter of the orifice at the nozzle end of the base. The previously described liquid parenteral medications, including stable non-aqueous suspensions, are suitable for jet injection in this manner.

In an embodiment of the injector device shown in FIGS. 9A–9D and 10A–10D, the hand force is applied directly to the second end 28 of the plunger. The plunger section may include a barrel 34, as in FIGS. 9A–9D, or the plunger may be a sliding fit in the cavity 46, as in FIGS. 10A–10B. In storage the second end of the plunger may be covered by a sterile outer cap 109, as in FIG. 10A.

Preferably the hand force may be applied to a cap 78, as in FIGS. 1–8 and 11A–11B. The cap is part of the plunger section 12. The cap telescopes over the base 14 and has a cross-sectional shape similar to that of the base. The cap may be semispherical, making it very comfortable to hold. Preferably the cap is generally cylindrical and cup-shaped, which takes up less space and requires less material to manufacture. A box shape may also be used. One of the advantages of the cap is that it lends itself to shapes which do not resemble a conventional syringe, helping to reduce anxiety.

The cap may have a central section 80 and a peripheral section 82. The central section 80 is generally planar and is preferably either flat or slightly convex. The central section has a periphery 84. The peripheral section 82 of the cap is attached to the periphery 84 of the central section 80. The peripheral section of the cap extends approximately perpendicular to the central section and toward the skin surface 16. Each of the central and peripheral sections has an outer surface 86 or 88 and an inner surface 90 or 92 respectively. The hand force is applied to the central section 80 of the cap 78, with the force vector being toward the skin surface. The inner surface 92 of the peripheral section of the cap contacts the outer surface 52 of the base. The moving portion of the plunger section 12 includes the cap.

An advantage of the cap is the comfortable fit of the injector in the palm of the vaccinator's hand. While thumb or finger pressure may be used to trigger the injector device, palm pressure activates it even more easily. This reduces fatigue in large vaccination campaigns.

In one preferred embodiment, the second end of the plunger is integrally attached to the central section of the cap. See FIGS. 1–4B and 11A–11B. This arrangement is simple, durable in transport, and inexpensive to manufacture. For a barrel in a "first end up" configuration, the cap may also be integrally attached to the barrel.

An alternative design is shown in FIGS. 5–7B. The cap 78 and the plunger 24 are not integrally attached. The inner surface 90 of the cap is near the second end 28 of the plunger. The motion of the moving portion of the plunger section toward the skin surface after the snap point is reached brings the inner surface 90 of the cap into contact with the second end 28 of the plunger. This contact drives the plunger toward the skin surface. The central section 80 of the cap may have a retaining projection 94 extending from the center of the inner surface 90 of the central section. The retaining projection is tubular and has a shape corresponding to that of the second end 28. The retaining projection 94 has an inner surface 96. The second end 28 of the plunger is adjacent to the inner surface of the retaining projection after the snap point is reached, as shown in FIGS. 6A–6C and 7B. The second end of the plunger is loosely held by the retaining projection.

Another suitable design is shown in FIG. 8. The plunger section includes a barrel 34. The barrel is between the first end 26 of the plunger 24 and the cap 78. The cap and the barrel are not integrally attached. The inner surface 90 of the central section of the cap is near the first end 36 of the barrel. The motion of the moving portion of the plunger section toward the skin surface after the snap point is reached brings the inner surface 90 of the central section into contact with the first end 36 of the barrel. The contact drives the barrel toward the skin surface. Since the liquid medication 32 inside the barrel is noncompressible, the plunger is also driven toward the skin surface until it is arrested by the second end 28 of the plunger contacting the nozzle end 54 of the cavity. The barrel continues to travel toward the skin surface, injecting the liquid medication through the plunger.

If an injection means involving either a hollow needle or a glass needle is used, preferably the injector device 10 includes a withdrawal mechanism for withdrawing the hollow needle, the shaft, or the like after the injection is complete. The withdrawal mechanism may be a gas spring, as shown in FIGS. 9A–9D. In this embodiment the cavity 46 is gas-tight, and the cavity contains a gas. The motion of the moving portion of the plunger section toward the skin surface after the snap point is reached compresses the gas within the cavity. The motion may be arrested by the compression, or the motion may be arrested by contact with the nozzle end of the cavity. After the injection is complete, expansion of the gas from its compressed state moves the moving portion of the plunger section back toward the initial position after injection of the parenteral medication. See FIG. 9D. The plunger section typically does not return to the initial position, but moves back far enough so that the free end 60 or 66 of the hollow needle or the shaft is within the bore.

Alternatively, the plunger section may includes a coil spring, leaf spring, or the like. The motion of the moving portion of the plunger section toward the skin surface after the snap point is reached is arrested by compression of the spring, and expansion of the spring after compression moves the moving portion of the plunger section back toward the initial position after injection of the parenteral medication. The coil spring 98 may be located within the cavity, as shown in FIGS. 1–2C and 4A. In this configuration, the coil spring preferably surrounds the hollow needle or the shaft. The coil spring 98 may also be located between the second end 28 of the plunger and the plunger end 48 of the base, as in FIGS. 3A–3C. If the plunger section includes a cap, the coil spring may be located between the inner surface 90 of the central section of the cap and the plunger end 48 of the base, as in FIGS. 3A–3C. The spring may surround the plunger, as in 3A–3C.

The snap means may have a break tab. Preferably the snap means has a plurality of break tabs. See FIGS. 1–6C. The break tabs are thin and frangible, and break at the snap point. Preferably the break tabs break when the hand force is at least 10 N but not more than 40 N; a range of 20–30 N is preferred.

If the injector device includes a cap, the break tabs may include one or more cap break tabs 100. The cap break tabs 100 project inward from the inner surface 92 of the peripheral section 82 of the cap when the plunger section is in the initial position. The break line is preferably where the cap break tab attaches to the inner surface 92. The cap break tabs 100 are adjacent to the plunger end 48 of the base when the plunger section is in the initial position. Preferably three to six break tabs are evenly distributed circumferentially around the cap.

The break tabs initially resist the movement of the plunger section when hand force is applied. The snap point occurs when the breaking strength of the break tabs is exceeded. When sufficient hand force is applied to the cap to reach the snap point, the break tabs break and allow the cap to travel rapidly toward the skin surface. The break tabs are preferably composed of plastic and are molded integrally with the cap. As a snap means, break tabs have the advantage of assuring that the injector device cannot be re-used. Break tabs also provide an easily reproducible snap point at a level of hand force which is comfortable for health workers.

The cap preferably includes a locking mechanism to prevent withdrawal of the cap from the base, as in FIGS. 1–8 and 11A–11B. The cap may have one or more grooves 102 between the cap break tabs and the free end 104 of the peripheral section 82. The outer surface 52 of the base has at least one base projection 106 near the plunger end 48 of the base. The base projection projects into the groove 102 when the plunger section is in the initial position. The base projection 106 is adapted to prevent the cap from being removed from the base, while allowing the cap to move in the other direction after the snap point is reached. The base projection is preferably a circumferential ring with a triangular cross-section, providing a ramp shape with the flat side toward the free end 104. A self-destruct base projection 118 may project from the outer surface 52 of the base near the nozzle end, as shown in FIGS. 7A–7B, preventing the cap from moving back towards the initial position and so preventing refilling after use.

If the plunger section includes a barrel 34, the break tabs may include one or more barrel break tabs 108. See FIGS. 1–2C, 4A–7B. The barrel break tabs 108 extend from the barrel outward toward the peripheral section of the cap when the plunger section is in the initial position. Preferably the barrel break tabs are integrally attached to the second end 38 of the barrel. In the initial position, the barrel break tabs hold the barrel in the proper position within the cavity. As hand force is applied to the plunger section, the barrel break tabs initially resist the motion, then break as their breaking strength is exceeded. The barrel is then free to move, and moves rapidly toward the skin surface. The barrel break tabs 108 may have the same break strength and break simultaneously with the cap break tabs, or one set of break tabs may break slightly before the other set. For example, the barrel break tabs may have a yield force lower than the cap break tabs.

FIGS. 1–2C show a complete injection sequence. In storage the nozzle end 50 of the base is covered by a sterile outer cap 109 of foil, thin plastic, or similar materials. The outer cap is removed just prior to use. The tapered nozzle 76 is applied to the cleaned deltoid area of the upper arm, or any alternative injection site such as the lateral thigh or buttock. The tapered nozzle seals against the skin. Hand force is applied to the cap 78. At the snap point, the cap break tabs 100 break, causing the barrel break tabs 108 to break. The cap, plunger, barrel, and hollow needle move toward the skin surface. The coil spring 98 is compressed between the barrel and the nozzle end 54 of the cylindrical cavity. The barrel's motion is arrested as it strikes the nozzle end 54, with the hollow needle 18 penetrating to its preset depth. Depth of penetration is adjusted by varying the degree of overshoot of the needle. The plunger continues to move, injecting the liquid medication through the hollow needle into the tissue. The injection is completed in less than a second, as the plunger reaches the first end 36 of the barrel. On the release of hand pressure, the needle is withdrawn by expansion of the spring.

Instead of break tabs, the snap means may include one or more snap rings, as in FIGS. 7A–11B. Rather than breaking at the snap point, the snap ring snaps past an opposing obstacle at the snap point. The snap ring may be a cap snap ring 110, as in FIGS. 7A–8. The cap snap ring extends inward from the inner surface 92 of the peripheral section of the cap. The outer surface 52 of the base may include a corresponding groove 102. The cap snap ring 110 projects into the groove 102 when the plunger section is in the initial position. Natural elasticity of the materials used in manufacturing the cap permit the snap ring to expand temporarily. The snap ring may be a ring-shaped ridge or annular bead similar to the bottle closures disclosed in U.S. Pat. No. 3,407,956 to Linkletter. In bottle caps and other similar closures, the sudden acceleration is immediately arrested by the cap seating itself. In the injector device 10, this acceleration is harnessed for generating injection pressures. An undesirable feature of snap rings is that they are inherently reusable, which may require other self-destruct or self-locking features to be added to prevent re-use.

The snap means may include a base snap ring 112, or both a cap snap ring 110 and a base snap ring. The base snap ring extends from the outer surface 52 of the base near the plunger end 48. If both a cap snap ring and a base snap ring are used, the cap snap ring 110 is adjacent to the base snap ring 112 when the plunger section is in the initial position. At the snap point the two snap past each other. One or more grooves 102 may also be provided into which the snap rings project. See FIGS. 7A–8.

The snap means may include a plunger snap ring 114, as in FIGS. 9A–10D. The plunger snap ring may attach to the plunger 24 and extends from the plunger toward the outer surface 52 of the base. Preferably the plunger snap ring is located near the first end 26 of the plunger. Alternatively, the plunger snap ring 114 is attached to the base near the plunger end 48 and extends from the base toward the plunger near the plunger end of the base. The plunger snap rings initially resist the motion of the plunger toward the skin surface. Eventually they are stretched too far and snap past each other, and the plunger moves rapidly toward the skin surface.

Preferably the base 14 has a peripheral space 116 between the cavity and the outer surface of the base. The cap 78 is preferably wide enough to push easily against with the fingers or hand. The peripheral space assures that the base is wide enough to fit easily into the cap, while reducing the materials used.

The injector device 10 provides a safe and inexpensive alternative to both conventional syringes with needles and to conventional jet injection devices. Since the dose is prefilled, errors in dosing and diluting are eliminated. The number of steps in giving an injection is greatly reduced, so that injections can be performed much more quickly. Sterility is assured, and cross-contamination is avoided. The anxiety and pain generally involved in injections are greatly reduced. For health workers, the risk of accidental needlesticks is reduced. The discarded syringes are not a health hazard, since no needle protrudes from the injector device after use.

It is to be understood that while specific embodiments of the present invention are described herein, the invention is not to be limited to such embodiments.

What is claimed is:

1. A single use injector device for injecting at least one parenteral medication into the body of a patient through a skin surface, the injector device operating by hand force, the injector device comprising:

a plunger section including a plunger, the plunger having a longitudinal axis, a first end, and a second end;

a base, the base being generally tubular and having a plunger end and a nozzle end, the base having a cavity and an outer surface, the cavity having a nozzle end and a longitudinal axis, the longitudinal axis of the cavity being coincident with the longitudinal axis of the plunger, the plunger being located at least partially within the cavity, the plunger sliding within the cavity parallel to the longitudinal axis of the cavity;

snap means for resisting movement of at least a moving portion of the plunger section from an initial position toward the skin surface as the hand force is applied to the moving portion of the plunger section, the snap means releasing the moving portion of the plunger section abruptly as a snap point is reached, the moving portion of the plunger section moving rapidly toward the skin surface after the snap point is reached, the snap means not including a spring; and injection means for injecting the medication, the motion of the moving portion of the plunger section toward the skin surface after the snap point is reached driving the parenteral medication through the skin surface and into the body of the patient.

2. The injector device according to claim 1, wherein:

at least a part of the parenteral medication is a liquid medication;

the plunger section includes a barrel, the barrel is tubular and has a first end and a second end, the first end is at least partially closed, the barrel has a reservoir adapted to contain the liquid medication, the barrel has a longitudinal axis coincident with the longitudinal axis of the plunger, the barrel has an inner surface and an outer surface, the barrel is located at least partially within the cavity, and the barrel slides within the cavity parallel to the longitudinal axis of the cavity;

the first end of the plunger is located within the barrel and is adapted to contact the liquid medication, the first end has a periphery, the periphery of the first end of the plunger forms a sliding seal with the inner surface of the barrel, the seal is liquid-tight, and the plunger slides with respect to the barrel parallel to the longitudinal axis of the plunger; and the motion of the moving portion of the plunger section toward the skin surface expels the liquid medication from the reservoir and injects the liquid medication into the body of the patient.

3. The injector device according to claim 2, wherein the moving portion of the plunger section includes the plunger and the barrel.

4. The injector device according to claim 3, wherein the first end of the barrel is located between the first end of the plunger and the nozzle end of the cavity.

5. The injector device according to claim 3, wherein the plunger is located between the first end of the barrel and the nozzle end of the cavity.

6. The injector device according to claim 1, wherein the moving portion of the plunger section includes the plunger, the first end of the plunger is located within the cavity, the cavity has a cavity surface, the first end of the plunger has a periphery, and the periphery of the first end of the plunger contacts the cavity surface.

7. The injector device according to claim 1, wherein the base includes a bore extending between the nozzle end of the cavity and the nozzle end of the base.

8. The injector device according to claim 7, wherein:

at least a part of the parenteral medication is a liquid medication, further comprising:

reservoir means for containing the liquid medication; and wherein:

the injection means includes a hollow needle, the hollow needle is tubular and has an attachment end and a free end, the attachment end is attached to the plunger section, the free end is sharp, the interior of the hollow needle is in fluid communication with the reservoir means, the free end of the hollow needle is located within the bore when the plunger section is in the initial position, and the motion of the moving portion of the plunger section after the snap point is reached drives the free end of the hollow needle through the skin surface, so that the liquid medication is expelled from the reservoir means through the hollow needle into the body of the patient.

9. The injector device according to claim 7, wherein:

the plunger section includes a shaft, the shaft has an attachment end and a free end, the shaft extends parallel to the longitudinal axis of the plunger and toward the skin surface, the free end of the shaft is blunt, and the free end of the shaft is located within the bore when the plunger section is in the initial position; and the injection means includes a glass needle, the glass needle is adapted to contain at least a part of the parenteral medication, the glass needle is located within the bore and between the shaft and the nozzle end of the base when the plunger section is in the initial position, and the motion of the moving portion of the plunger section after the snap point is reached drives the shaft toward the skin surface through the bore, the free end of the shaft striking the glass needle and driving the glass needle through the skin surface, so that the glass needle remains in the body of the patient and dissolves in the body of the patient.

10. The injector device according to claim 9, wherein the shaft is solid.

11. The injector device according to claim 9, wherein the shaft is tubular.

12. The injector device according to claim 11, wherein:

a part of the parenteral medication is a liquid medication; further comprising:

reservoir means for containing the liquid medication; and wherein:

the interior of the shaft is in fluid communication with the reservoir means, and the motion of the moving portion of the plunger section after the snap point is reached drives the free end of the shaft through the skin surface after the glass needle, so that the liquid medication is expelled from the reservoir means through the shaft and into the body of the patient after the glass needle.

13. The injector device according to claim 12, wherein:

the liquid medication is contained in the cavity; and the shaft includes at least one perforation near the attachment end of the shaft, the interior of the shaft is in fluid communication with the cavity through the perforation.

14. The injector device according to claim 7, wherein:

at least a part of the parenteral medication is a liquid medication; further comprising:

reservoir means for containing a part of the liquid medication; and wherein:

at least a part of the liquid medication is contained in the bore, and the bore is in fluid communication with the reservoir means; and the injection means includes jet injection means for injecting the liquid medication in the form of a liquid jet, the motion of the moving portion of the plunger section after the snap point is reached increases the pressure of the liquid medication within the reservoir means and the bore to form the liquid jet, and the liquid medication is expelled from the reservoir means through the bore and into the body of the patient.

15. The injector device according to claim 14, wherein:

the plunger section includes a shaft, the shaft has an attachment end and a free end, the shaft extends parallel to the longitudinal axis of the plunger and toward the skin surface, the shaft is tubular and has a free end, the free end of the shaft is located within the bore when the plunger section is in the initial position;

the bore has a nozzle end, the nozzle end of the bore includes a sealing membrane, and the bore includes a seal surrounding the shaft, the seal being liquid-tight; and the nozzle end of the base includes a tapered nozzle.

16. The injector device according to claim 1, wherein the hand force is applied to the second end of the plunger.

17. The injector device according to claim 1, wherein the plunger section includes a cap, the cap has a central section and a peripheral section, the central section is generally planar and has a periphery, the peripheral section is attached to the periphery of the central section and extends approximately perpendicular to the central section and toward the skin surface, each of the central and peripheral sections has an outer surface and an inner surface, the hand force is applied to the central section of the cap, the inner surface of the peripheral section of the cap contacts the outer surface of the base, and the moving portion of the plunger section includes the cap.

18. The injector device according to claim 17, wherein the central section of the cap is flat.

19. The injector device according to claim 17, wherein the second end of the plunger is integrally attached to the central section of the cap.

20. The injector device according to claim 17, wherein the cap and the plunger are not integrally attached, the inner surface of the cap is near the second end of the plunger, the motion of the moving portion of the plunger section toward the skin surface after the snap point is reached brings the inner surface of the cap into contact with the second end of the plunger, and the contact of the inner surface of the cap and the second end of the plunger drives the plunger toward the skin surface.

21. The injector device according to claim 20, wherein the central section of the cap has a retaining projection extending from the inner surface of the central section, the retaining projection is tubular and has an inner surface, and the second end of the plunger is adjacent to the inner surface of the retaining projection after the snap point is reached.

22. The injector device according to claim 17, wherein:

at least a part of the parenteral medication is a liquid medication;

the plunger section includes a barrel, the barrel is tubular and has a first end and a second end, the first end is at least partially closed, the barrel has a reservoir adapted to contain the liquid medication, the barrel has a longitudinal axis parallel to the longitudinal axis of the plunger, the barrel has an inner surface and an outer surface, the barrel is located at least partially within the cavity, and the barrel slides within the cavity parallel to the longitudinal axis of the cavity;

the first end of the plunger is located within the barrel and is adapted to contact the liquid medication, the first end has a periphery, the periphery of the first end of the plunger forms a sliding seal with the inner surface of the barrel, the seal is liquid-tight, and the plunger slides with respect to the barrel parallel to the longitudinal axis of the plunger; and the motion of the moving portion of the plunger section toward the skin surface expels the liquid medication from the reservoir and injects the liquid medication into the body of the patient.

23. The injector device according to claim 22, wherein the barrel is between the first end of the plunger and the cap, the cap and the barrel are not integrally attached, the inner surface of the cap is near the first end of the barrel, the motion of the cap toward the skin surface after the snap point is reached brings the inner surface of the cap into contact with the first end of the barrel, and the contact of the inner surface of the cap and the first end of the barrel drives the barrel toward the skin surface.

24. The injector device according to claim 1, wherein the cavity is gas-tight, the cavity contains a gas, the motion of the moving portion of the plunger section toward the skin surface after the snap point is reached compresses the gas within the cavity, and expansion of the gas after compression moves the moving portion of the plunger section back toward the initial position after injection of the parenteral medication.

25. The injector device according to claim 1, wherein the plunger section includes a spring, the motion of the moving portion of the plunger section toward the skin surface after the snap point is reached compresses the spring, and expansion of the spring after compression moves the moving portion of the plunger section back toward the initial position after injection of the parenteral medication.

26. The injector device according to claim 25, wherein the spring is a coil spring.

27. The injector device according to claim 26, wherein the coil spring is located within the cavity.

28. The injector device according to claim 26, wherein the coil spring is located between the second end of the plunger and the plunger end of the base.

29. The injector device according to claim 1, wherein the snap means includes at least one break tab, and the break tab is frangible.

30. The injector device according to claim 29, wherein the break tab breaks when the hand force is at least 10 N but not more than 40 N.

31. The injector device according to claim 29, wherein:
the plunger section includes a cap, the cap has a central section and a peripheral section, the central section is generally planar and has a periphery, the peripheral section is attached to the periphery of the central section and extends approximately perpendicular to the central section and toward the skin surface, each of the central and peripheral sections has an outer surface and an inner surface, the hand force is applied to the central section of the cap, and the moving portion of the plunger section includes the cap; and
the break tab includes at least one cap break tab, and the cap break tab projects from the inner surface of the peripheral section of the cap.

32. The injector device according to claim 31, wherein the cap break tab is adjacent to the plunger end of the base when the plunger section is in the initial position.

33. The injector device according to claim 32, wherein the peripheral section of the cap has a free end, the cap has at least one groove between the cap break tab and the free end of the peripheral section, the outer surface of the base has at least one base projection near the plunger end of the base, the base projection projects into the groove when the plunger section is in the initial position, and the base projection is adapted to prevent the cap from being removed from the base.

34. The injector device according to claim 32, wherein:
at least a part of the parenteral medication is a liquid medication;
the plunger section includes a barrel, the barrel is tubular and has a first end and a second end, the first end is at least partially closed, the barrel has a reservoir adapted to contain the liquid medication, the barrel has a longitudinal axis parallel to the longitudinal axis of the plunger, the barrel has an inner surface and an outer surface, the barrel is located at least partially within the cavity, and the barrel slides within the cavity parallel to the longitudinal axis of the cavity;
the first end of the plunger is located within the barrel and is adapted to contact the liquid medication, the first end has a periphery, the periphery of the first end of the plunger forms a sliding seal with the inner surface of the barrel, the seal is liquid-tight, and the plunger slides with respect to the barrel parallel to the longitudinal axis of the plunger; and
the motion of the moving portion of the plunger section toward the skin surface expels the liquid medication from the reservoir and injects the liquid medication into the body of the patient.

35. The injector device according to claim 34, wherein the break tab includes at least one barrel break tab, and the barrel break tab extends from the barrel toward the peripheral section of the cap when the plunger section is in the initial position.

36. The injector device according to claim 1, wherein the snap means includes at least one snap ring.

37. The injector device according to claim 36, wherein:
the plunger section includes a cap, the cap has a central section and a peripheral section, the central section is generally planar and has a periphery, the peripheral section is attached to the periphery of the central section and extends approximately perpendicular to the central section and toward the skin surface, each of the central and peripheral sections has an outer surface and an inner surface, the hand force is applied to the central section of the cap, and the moving portion of the plunger section includes the cap.

38. The injector device according to claim 37, wherein the snap means includes a cap snap ring, and the cap snap ring extends from the inner surface of the peripheral section of the cap.

39. The injector device according to claim 37, wherein the snap means includes a base snap ring, the base snap ring extends from the outer surface of the base near the plunger end of the base.

40. The injector device according to claim 36, wherein the snap means includes a plunger snap ring, the plunger snap ring is attached to the plunger and extends from the plunger toward the outer surface of the base, and the plunger snap ring is located near the first end of the plunger.

41. The injector device according to claim 36, wherein the snap means includes a plunger snap ring, the plunger snap ring is attached to the base and extends from the base toward the plunger, and the plunger snap ring is located near the plunger end of the base.

42. The injector device according to claim 1, wherein the injection means includes a glass needle.

43. The injector device according to claim 42, wherein the glass needle is composed at least partially of a glass selected from the group consisting of sugar glass, trehalose glass, trehalose octaacetate glass, glucose pentaacetate glass, silica glass, phosphate glass, metal carboxylate glass, and mannitol glass.

44. The injector device according to claim 43, wherein at least a part of the parenteral medication is incorporated into the glass.

45. The injector device according to claim 43, wherein the glass needle is tubular, and at least a part of the parenteral medication is contained in the interior of the glass needle.

46. The injector device according to claim 1, wherein the base and the plunger section are at least partially composed of plastic.

47. The injector device according to claim 46, wherein the base and the plunger section are composed of plastic.

48. The injector device according to claim 1, wherein:

the first end of the plunger is narrow, the cavity extends from the plunger end of the base to the nozzle end of the base, the first end of the plunger is blunt, and the first end of the plunger is located within the cavity when the plunger section is in the initial position; and the injection means includes a glass needle, the glass needle is adapted to contain the parenteral medication, the glass needle is located within the cavity and between the plunger and the nozzle end of the base when the plunger section is in the initial position, and the motion of the moving portion of the plunger section after the snap point is reached drives the first end of the plunger toward the skin surface through the cavity, the first end of the plunger striking the glass needle and driving the glass needle through the skin surface, so that the glass needle remains in the body of the patient and dissolves in the body of the patient.

49. The injector device according to claim 1, wherein:

at least a part of the parenteral medication is a liquid medication; and at least a part of the liquid medication is a suspension in perfluorocarbon.

* * * * *